(12) United States Patent
Lihme et al.

(10) Patent No.: US 6,627,460 B1
(45) Date of Patent: Sep. 30, 2003

(54) METHOD FOR PREPARING WATER-SOLUBLE CROSS-LINKED CONJUGATES

(75) Inventors: Allan Otto Fog Lihme, Birkerod (DK); Christopher John Stanley, Cambridgeshire (GB)

(73) Assignee: Amdex A/S, Jyllinge (DK)

( * ) Notice: Subject to any disclaimer, the term of this patent is extended or adjusted under 35 U.S.C. 154(b) by 0 days.

(21) Appl. No.: 09/743,637

(22) PCT Filed: Jul. 29, 1999

(86) PCT No.: PCT/DK99/00426
§ 371 (c)(1),
(2), (4) Date: Apr. 5, 2001

(87) PCT Pub. No.: WO00/07019
PCT Pub. Date: Feb. 10, 2000

(30) Foreign Application Priority Data

Jul. 30, 1998 (DK) .................... PA 1998 00992

(51) Int. Cl.[7] ............ G01N 33/548; G01N 33/552; G01N 33/532; C07K 1/13; C07K 17/06; C07K 17/10; C07K 17/12
(52) U.S. Cl. ............ 436/529; 436/527; 436/530; 436/544; 436/823; 530/391.1; 530/391.5; 530/408
(58) Field of Search ............ 436/529, 823, 436/530, 542, 527, 544; 530/391.1, 391.5, 408; 435/7.92, 6

(56) References Cited

U.S. PATENT DOCUMENTS

| 5,466,609 A | 11/1995 | Siiman et al. ............ 436/518 |
| 5,527,713 A | 6/1996 | Bolton et al. ............ 436/529 |
| 5,891,741 A | 4/1999 | Siiman et al. ............ 436/529 |

FOREIGN PATENT DOCUMENTS

| EP | 0 291 194 | 11/1988 |
| EP | 0 594 772 | 8/1996 |
| WO | 98/52040 | 11/1998 |

OTHER PUBLICATIONS

K. Knudsen et al, Analytical Biochemistry, vol. 201, 170–177 (1992).*

A. Lihme et al., "Divinylsulphone–Activated Agarose: Formation of Stable and Non–Leaking Affinity Matrices by Immobilization of Immunoglobulins and Other Proteins.", Journal of Chromatography, vol. 347, pp. 299–305, 1986, XP–002122286.

Olavi Siiman et al., "Fluorescent Neoglycoproteins: Antibody–Aminodextran–Phycobiliprotein Conjugates.", Bioconjugate Chem. vol. 10, No. 6, pp. 1090–1106.

* cited by examiner

Primary Examiner—Mary E. Ceperley
(74) Attorney, Agent, or Firm—Foley & Lardner

(57) ABSTRACT

A novel preparative methodology yields water-soluble, cross-linked conjugates and conjugate complexes that confer an improved sensitivity in immunochemical assays, particularly in the context of lateral flow devices and in determinations of the presence or absence of small amounts of active components present in a liquid sample.

25 Claims, 6 Drawing Sheets

METHOD FOR PREPARING WATER-SOLUBLE CROSS-LINKED CONJUGATES

FIELD OF THE INVENTION

The present invention relates to novel methods for the preparation of water-soluble cross-linked conjugates and conjugate complexes as well as to novel water-soluble cross-linked conjugates and conjugate complexes per se. The conjugates and conjugate complexes confer an improved sensitivity in immunochemical assays, in particular when used in lateral flow devices and in methods for determining the presence or absence of small amounts of active components present in liquid samples.

BACKGROUND OF THE INVENTION

A large research effort has been devoted to devising ways to improving immunochemical assay reliability and sensitivity in e.g. home pregnancy and fertility tests and, consequently, there is a continuous need for new and improved methods for preparing conjugates which exhibit a high degree of sensitivity and specificity when employed in such immunochemical assays. Clearly, the number of "active" components, such as the number of antibodies or antigens, and the number of "detectable units", such as dye molecules, present in the conjugate are of utmost importance when developing new conjugates for use in high-sensitive immunochemical assays.

Various strategies for improving the sensitivity and reliability of immunoassays have been reviewed by L. J. Kricka (1994) *Clin. Chem.* 40, 347–357.

EP 0 594 772 B1 relates to water-soluble, polymer-based conjugates comprising moieties derived from divinyl sulfone. EP 0 594 772 B1 describes the possibility of enhancing the attachment of molecular species, such as antibodies and antigens, to a water-soluble carrier molecule by taking advantage of the so-called "salting out" effect. It turned out, however, that by increasing the salt concentration to about 1 M an irreversible precipitate was formed.

It has now surprisingly been found that by further increasing the concentration of salt in the reaction mixture, a reversible (i.e. a re-dissolvable) precipitate is formed which contains "large" water-soluble conjugates which are useful in various immunochemical assays, such as in lateral flow devices.

DESCRIPTION OF THE INVENTION

In a first aspect the present invention relates to a method for the preparation of a water-soluble cross-linked conjugate comprising moieties of at least one carrier component, moieties of more than one linking component, moieties of at least one spacer component, moieties of at least one signal component and moieties of at least one primary targeting component, the signal component being covalently attached to the spacer component and the spacer component being covalently attached, via the linking component, to the carrier component, said method comprising:

a) reacting a water-soluble intermediate conjugate comprising moieties of at least one carrier component, moieties of more than one linking component, moieties of at least one spacer component, moieties of at least one signal component, the signal component being covalently attached to the spacer component and the spacer component being covalently attached, via the linking component, to the carrier component, via reaction of unreacted reactive moieties derived from the linking component, with at least one primary targeting component in an aqueous solution, the conditions being such that a reversible precipitate is formed;

b) re-dissolving the reversible precipitate comprising the water-soluble cross-linked conjugate in an aqueous medium; and c) optionally subjecting the water-soluble cross-linked conjugate to a purification step.

In the present context the term "water soluble" when used in connection with the cross-linked conjugates means that the conjugates obtained according to the methods disclosed herein should be soluble in an aqueous medium, such as water, at room temperature, i.e. the cross-linked conjugates obtained by the methods disclosed herein should give rise to a solution which is substantially clear and homogenous as judged by visual inspection of the sample.

In a preferred embodiment of the invention the cross-linked conjugates obtained by the methods disclosed herein have a water solubility of at least 0.1, preferably at least 1, such as at least 10, more preferably at least 50, such as at least 100, in particular at least 200 mg dry conjugate per ml water at 25° C.

Before going into a detailed discussion with respect to the above-mentioned precipitation step, it should be noted that the water-soluble intermediate conjugate may be prepared by a method comprising:

I) reacting at least one water-soluble carrier component with more than one linking component in an aqueous solution at a pH above 7, so as to form an aqueous solution containing a water-soluble intermediate precursor comprising water-soluble moieties of the carrier component having covalently attached thereto reactive moieties derived from the linking component;

II) optionally subjecting the water-soluble intermediate precursor to a purification step;

III) reacting the optionally purified water-soluble intermediate precursor, via reaction of said reactive moieties, with i) at least one spacer component in an aqueous solution at a pH above 7, so as to form a second water-soluble intermediate precursor, the conditions being such that only a fraction of the reactive moieties reacts with the spacer component and that a significant amount of unreacted reactive moieties remain, ii) optionally subjecting the second water-soluble intermediate precursor to a purification step, and iii) reacting the optionally purified second water-soluble intermediate precursor, via reaction of the spacer component, with at least one signal component in an aqueous solution at a pH above 7, so as to form a water-soluble intermediate conjugate, the conditions being such that most of the signal components react with the spacer moiety, rather than with the linker component, and that a significant amount of unreacted reactive moieties of the linker component remain unreacted ( i.e. only a small fraction of the signal components react with the reactive moieties of the linker components); and IV) optionally subjecting the water-soluble intermediate conjugate obtained in step III) to a purification step.

The method outlined in general form above in steps I–IV, and the components alluded to therein, is schematically represented in FIG. 4. The Figure is merely to be used for purposes of clarity as it represents anecdotal examples of one embodiment. Therein, the various stages of intermediates and precursors that are part of the method are schematically represented to assist the reader to follow the procedure.

The Water-Soluble Carrier Component

The term "carrier component" in the context of the present invention is used to denote the "backbone" of the conjugate, i.e. the carrier component functions as a backbone on which various molecules may be attached.

The water-soluble polymers which function as the carrier component in the method for the preparation of conjugates may be chosen from a wide variety of types of polymers, including:

natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid;

homopoly(amino acid)s having suitable reactive functionalities, such as polylysines, polyhistidines or polyornithines;

natural and synthetic polypeptides and proteins, such as bovine serum albumin and other mammalian albumins; and synthetic polymers having nucleophilic functional groups, such as polyvinyl alcohols, polyallyl alcohol, polyethylene glycols and substituted polyacrylates.

Very suitable polymers for the purposes of the invention are polysaccharides and derivatives thereof, for example: dextrans, carboxymethyl-dextrans, hydroxyethyl- and hydroxypropyl-starches, glycogen, agarose derivatives, and hydroxyethyl- and hydroxypropyl-celluloses. As will be apparent from the working examples herein (vide infra), notably dextrans have proved to be particularly suitable polymers in connection with the invention, and they are presently the most preferred carrier components.

As already indicated, it is often desirable, particularly for many of the immunochemical applications of the conjugates, that said conjugates have no, or substantially no, net charge, since the presence of a net positive or negative charge in such cases can lead, inter alia, to undesirable non-specific binding of the conjugates to substances and/or materials other than those of interest. In many cases this condition will, unless charged species are introduced, be fulfilled simply by ensuring that the polymeric carrier component itself possesses no net charge. Thus, a preferred polymeric carrier component for use in the method of the invention is, in its free state, substantially linear and substantially uncharged at a pH in the range of about 4 to about 10, the latter pH interval being the interval of practical relevance for the vast majority of immunochemical procedures, hybridisation procedures and other applications of conjugates. Among various polymers which meet this criterion, are, for example, numerous polysaccharides and polysaccharide derivatives, e.g. dextrans and hydroxyethyl- and hydroxypropylcelluloses.

Depending on the use to which a conjugate is to be put, the conjugates may be based on water-soluble polymeric carrier components having a range of molecular weights. In one embodiment of the invention, the polymeric carrier component may have a peak molecular weight in the range of about 40,000 to about 40,000,000 (prior to reacting said water-soluble polymeric carrier components with linker reagent such as DVS or EPCH, or reacting resulting water-soluble intermediate precursor with a spacer or signal component for the eventual formation of cross-linked conjugate and cross-linked conjugate complexes). Peak molecular weights which are of considerable interest are peak molecular weights in the range of 100,000 to 10,000,000, such as in the range from 500,000 to 8,000,000, preferably in the range from 500,000 to 4,000,000, e.g. in the range from 500,000 to 2,000,000. Peak molecular weights of particular interest, notably in the case of dextrans as polymeric carrier components, are peak molecular weights of about 500,000, about 1,000,000, about 1,500,000, about 2,000,000, 2,500,000, about 3,000,000, about 3,500,000 and about 4,000,000.

More particularly, dextrans in the molecular weight ranges of 20,000 to 2,000,000 are preferred as starting carrier components. Most particularly, 20,000 Da dextrans are preferred for, but not restricted to, conjugates and/or complexes using streptavidin as the primary or secondary target. Furthermore, 500,000 Da dextrans are preferred for, but not restricted to, conjugates and/or complexes using certain dyes, enzymes, and with certain specific binding molecules as the primary or secondary target. Moreover, 2,000,000 Da dextrans are preferred for, but not restricted to, certain other dyes.

The term "peak molecular weight" as employed in the present specification and claims in connection with the carrier components denotes the molecular weight of greatest abundance, i.e. that molecular weight, among a distribution of molecular weights, which is possessed by the greatest number of molecules in a given sample or batch of the polymer. It is quite normal to characterise numerous types of polymers in this manner, owing to the difficulty (particularly for the highest molecular weights) of obtaining or preparing polymer fractions of very narrow molecular weight distribution. In the case of numerous commercially available carrier components which are of interest in the context of the invention, for example dextrans, the manufacturer or distributor will be able to provide reliable peak molecular weight data (determined, for example, by gel-permeation chromatography) which can provide a basis for the selection of the proper fraction of the polymeric carrier component. It should be mentioned here that peak molecular weight values (when used in connection with the carrier component) cited in the present specification and claims refer to the peak molecular weight of the free polymer in question, and take no account of, for example, the possible formation of cross-linked polymer units, e.g. as a result of cross-linking of two or more polymer molecules by reaction with a linking component such as DVS or EPCH during a method for the preparation of a conjugate; such cross-linked units will, on average, have higher molecular weights than the individual free polymer molecules from which they are formed.

Formation of the Water-Soluble Intermediate Precursor

In the present context the "term linking component" is intended to cover bi-functional molecules capable of establishing covalent links between other—typically larger—molecules. Examples of linking components suitable for the method according to the invention are e.g. molecules comprising a bi-functional reactivity such as glutaraldehyde, carbodiimides, N,N'-phenylenedimaleimide, N-succinimidyl 3-(2-pyridylthio)propionate, p-benzoquinone, bis oxiranes, divinyl sulfone (DVS) and epoxide derivatives, such as epoxides of the general formula I:

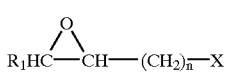

(I)

wherein $R_1$ is hydrogen or $C_{1-4}$-alkyl, n is an integer in the range from 1–4, i.e. 1, 2, 3 or 4, and X is a leaving group such as tosyl, mesyl, or halogen such as fluorine, chlorine, bromine, or iodine, preferably chlorine.

In the present context the term "$C_{1-4}$-alkyl" designates a straight or branched saturated hydrocarbon group having from 1 to 4 carbon atoms, such as methyl ethyl, n-propyl, n-butyl, isopropyl, isobutyl, etc.

As will be apparent from the working examples provided herein a very promising epoxide-derived linking component is epichlorohydrin (EPCH), i.e. a compound of the general formula I above, wherein $R_1$ is hydrogen, n is 1 and the leaving group X is chlorine.

Preferably, the linking component should be stable in an aqueous environment and, accordingly, the linking component EPCH constitutes together with the linking component DVS the presently most preferred linking components for use in the method of the invention.

The first step, i.e. step I), wherein the water-soluble intermediate precursor is formed, is conveniently carried out in an aqueous solution at a pH above 7, such as above 8.5, in particular above 9, such as above 10, for example at a pH around 10, 10.5, 11 or 11.5. In its most general form, the reaction may take place at a temperature in the range of 0–60° C., although a temperature in the range of 20–25° C. will often be quite suitable, as illustrated, for example, for carrier components such as dextrans, in the working examples given herein. In a preferred embodiment of the invention, the pH at which the reaction takes place is generally within the range of about 10–11.5, which is a pH range in which the reactive functionalities on most types of carrier components are reactive towards the presently preferred linking components DVS and EPCH.

As far as the concentration of the carrier component in the aqueous solution is concerned, it will generally be within the range of 0.1–20% w/v, and often in the range of 0.5–10% w/v, such as in the range of 0.5–5% w/v, in particular in the range from 0.5–2% w/v, such as about 0.5% w/v, about 1% w/v, about 1.5% w/v or about 2% w/v. The concentration of linking component in the aqueous solution will generally be in the range of 0.1–35% v/v, depending on the actual linking component employed. The concentration of the presently preferred linking components, i.e. DVS and EPCH, in the aqueous solution is typically in the range from 0.1–15% v/v in the case of DVS, and often in the range of 1–10% v/v. In the case of EPCH the concentration is typically in the range from 1–30% v/v, and often in the range from 3–20% v/v. In case the where the reagent for the preparation of the linking component is a solid, it is contemplated that the concentration will generally be in the range of 0.1–10% w/v.

It is difficult to give general guidelines concerning the period of time for which the reaction of linking component with the carrier component in the aqueous solution should be allowed to proceed, since these will vary rather considerably, depending on, e.g., the temperature and pH at which the reaction occurs, the concentration of the carrier component and the concentration of linking component in the reaction mixture, the nature and/or molecular weight of the carrier component and the nature of the linking component, and the extent to which cross-linking of the carrier (e.g. by reaction with DVS) may proceed before there is a risk, for example, of gelling or precipitation taking place.

The reaction time in question will, however, normally be within the range of 5 minutes to 10 hours. As will be apparent from the working examples provided herein, the reaction time required when DVS is used as the linking component is typically in the range from 5 to 120 minutes, such as in the range from 15 to 60 minutes, e.g. about 30 minutes, whereas activation of the carrier component with EPCH in general requires a longer reaction time, typically in the range from 1 to 10 hours, such as in the range from 3 to 7. hours, e.g. about 5 hours.

As already discussed, the carrier component in the water-soluble intermediate precursor has covalently attached thereto one or more moieties derived from a bifunctional linking component, each of which moieties is attached via a covalent linkage formed between one of the two functional groups of the bifunctional linking component and a reactive functionality on the carrier component. As will be understood, the remaining functional group of the bi-functional linking component will be free ("dangling") and, consequently, be capable of reacting with e.g. primary targeting components, spacer components and/or signal components under suitable conditions (vide infra).

The "load", i.e. the number of linking groups attached to the carrier component [in step I)], will typically be in the range from about 1 to about 5,000 moles of linking components per gram of carrier component, such as in any of the following sub-ranges (expressed as $\mu$moles linking component per gram of carrier component): about 1 to about 50; about 50 to about 300; about 300 to about 1,000; or about 1,000 to about 5,000. The number of linking groups attached to the carrier component may be determined by titration methods known per se, e.g. by the thiosulphate titration method described in Porath et al. (1975) *J. Chromatogr.* 103, 49. As is apparent from examples provided herein, the typical "load" of the linker, expressed in $\mu$moles of linker per gram of carrier ranges from approximately 300 to more than 2000. Thus, in preferred embodiments of this aspect of the invention, the range of about 1 to about 5,000 moles of linking components per gram of carrier component should particularly be between 200 and 3000, preferably between 500 and 2500.

The optional purification step (step II) may, for example, involve a process such as dialysis (for the removal of excess reagent or other species of low molecular weight) or some chromatographic technique which will be suitable for the purpose, such as gel-filtration. It should be understood, however, that the above-mentioned purification methods are only mentioned as examples and the skilled person will be able to select the most appropriate purification method in each individual case, which may depend on the actual conditions employed in the coupling step, the actual ingredients used in the coupling step as well as available equipment at the site of production.

Carrier components (which, as explained above, constitute the "backbone" of the conjugates) which are suitable for use in the method of the invention are preferably initially non-cross-linked and are of essentially zero charge at pH values which are of relevance within the fields of application of the invention.

Owing to the nature of the coupling chemistry employed in the method according to the invention, i.e. the establishment, on the carrier component, of covalently bound reactive moieties deriving from bi-functional molecules, such as DVS and EPCH, will generally require that a reactive functionality, preferably a nucleophilic functionality, is present on the carrier component. Suitable carrier components will then be, for example, polymeric carrier components with functional groups such as: —O$^-$ (e.g. deprotonated phenolic hydroxy groups, such as deprotonated aromatic hydroxy groups in tyrosine residues of polypeptides or proteins), —S$^-$ (e.g. deprotonated thiol groups on aromatic rings or aliphatic groups, such as deprotonated thiol groups in cysteine residues of polypeptides or proteins), —OH (e.g. aliphatic hydroxy groups on sugar rings, such as glucose or other monosaccharide rings in oligo- or polysaccharides; or alcoholic hydroxy groups in polyols, such as polyvinyl alcohol; or hydroxy groups in certain amino acid residues of polypeptides or proteins, such as serine or threonine residues), —SH (e.g. thiol groups in cysteine residues of polypeptides or proteins), primary amino groups (e.g. in lysine or ornithine residues of polypeptides or proteins; or in amino-substituted sugar rings in certain polysaccharides or derivatives thereof, such as chitosan) or secondary amino groups (e.g. in histidine residues of polypeptides or proteins). As will be understood by the skilled person, the question of whether the functional groups mentioned above will be in a protonated or de-protonated state will, of course, depend on the selected reaction conditions, such as the pH of the reaction mixture.

For similar reasons, the functional group in question on targeting components and spacer components (vide infra) in the context of the invention will also normally be a nucleophilic functionality, such as a nucleophilic functionality of one of the above-described types.

Formation of the Second Water-Soluble Intermediate Precursor

In step IIIi) of the method of the invention the spacer component is, via reaction with the linking component, covalently attached to the water-soluble intermediate precursor, thereby forming a second water-soluble intermediate precursor.

As indicated above, the "spacer component" is covalently attached, via the linking group, to the carrier component. Thus, the term "spacer component" when used in the present context is intended to mean a protein or a polypeptide which has a plurality of sites available for covalent attachment of signal components, such as dyes (vide infra).

One purpose for the incorporation of a spacer component, and particularly for a spacer having a plurality of sites available for covalent attachment of signal components, is that this method provides for a suitable means of increasing the number of signal components which can be attached to the conjugate (i.e. the "load" of the signal component in the water-soluble intermediate conjugate, vide ante), and thereby increasing the sensitivity of such conjugates when employed in various assays, e.g. immunochemical assays and in the lateral flow devices described herein (vide infra). It should be understood that in an embodiment wherein the coupling of a signal component (such as a dye molecule) is done directly to the linking component (and not through a spacer component) implies that (at least in principle) only one signal molecule is attached per molecule of linking component present in the conjugate.

In several embodiments of the preparation of the second water-soluble precursor, the number of moles of spacer per mole of starting dextran (the "load" of the spacer) ranges from 1 to 500, particularly from 2 to 100, most frequently from 5 to 75. Also, as explained in details in Example 3A herein, the second water-soluble intermediate (and hence the efficiency of the reaction carried out in step IIIi)) may be characterised by e.g. the number (moles) of spacer component attached per mole carrier component.

As stated earlier, only a fraction of the reactive moieties of the linking component of the water-soluble intermediate reacts with the spacer component. Depending on the spacer component and on the linker component, after reacting the spacer component, from 1 to 99% of the unreacted reactive moieties of the linker component, preferably 20-99%, particularly 30–99%, such as ranging from 40 to 99% and notably 50 to 99% remain unreacted. That is to say that, in one embodiment, under certain conditions, from 1 to 49% of the unreacted linker moieties reacted with the spacer component.

Preferably, the spacer component is a protein such as BSA, ovalbumin, globulin, etc. or a polypeptide such as homopolypeptides, e.g. polylysines, polyhistidines, polyornithines, etc. However, as will be clear to a person skilled in the art, the choice of spacer component will depend on the employed signal component (e.g. the actual dye employed in a particular conjugate) as well as the employed linking component.

The molecular weight of the spacer component, e.g. a protein, is preferably at least 10,000 Da, preferably in the range of 10,000–2,000,000, such as in the range of 20,000–500,000. As the one of the features of the introduced spacer components is to multiply the number of available positions for introduction of the signal components, it is furthermore preferred that the number of available functional groups for attachment of signal components is at least 5 per molecule of spacer component, preferably 10–1,000, in particular 10–500.

Alternatively, the spacer component can be a polysaccharide or polynucleic acid. Chemical modifications of these polymers may be required prior to the preparation of the water-soluble intermediate conjugate.

As stated earlier, owing to the nature of the coupling chemistry on the spacer component, (to both the linker component in the formation of the second water-soluble intermediate precursor, or later to a signal component in the formation of the water-soluble-intermediate conjugate, vide infra), a reactive functionality, such as a nucleophilic functionality, is present on the spacer component. Suitable spacer components will then be, for example, those with nucleophilic functional groups such as: —O⁻ (e.g. deprotonated phenolic hydroxy groups, such as deprotonated aromatic hydroxy groups in tyrosine residues of polypeptides or proteins), —S⁻ (e.g. deprotonated thiol groups on aromatic rings or aliphatic groups, such as deprotonated thiol groups in cysteine residues of polypeptides or proteins), —OH (e.g. aliphatic hydroxy groups present in certain amino acid residues of polypeptides or proteins, such as serine or threonine residues), —SH (e.g. thiol groups in cysteine residues of polypeptides or proteins), primary amino groups (e.g. in lysine or ornithine residues of polypeptides or proteins) or secondary amino groups (e.g. in histidine residues of polypeptides or proteins). As will be understood by the skilled person, the question of whether the functional groups mentioned above will be in a protonated or de-protonated state will, of course, depend on the selected reaction conditions, such as the pH of the reaction mixture.

Step IIIi) of the method of the invention, wherein the second water-soluble intermediate precursor is formed, is conveniently carried out in aqueous solution at a pH above 7, such as above 8, in particular above 9, such as above 10, for example at a pH in the interval of from 10 to 11, e.g. of from 10 to 10.5. It will normally be quite sufficient to carry out the reaction at a temperature in the range from 0–60° C., the optimal temperature being dependent on, inter alia, the actual pH employed. In most cases, especially when the reaction is carried out at a pH above 9, and in particular when the reaction is carried out at a pH above 10, a temperature in the range of 20–40° C., e.g. around 30° C., will often be quite suitable. With respect to the reaction time, it should be understood that several parameters will influence the reaction time required. Thus, depending on the employed pH, the reaction temperature, the concentration of peptide or polypeptide spacer component and the concentration of water-soluble intermediate precursor, the reaction time may vary within wide limits. It is contemplated, however, that a suitable reaction time will generally be in the range of from 1 hour to 48 hours and, as will be understood from the examples provided herein, the present inventors have found that by using the specified set of reaction conditions disclosed in Examples 3A and 3B, a reaction time in the range of from 10 to 30 hours, e.g. in the range from 15 to 25 hours such as about 18 hours, is quite suitable.

As stated earlier, only a fraction of the unreacted reactive moieties of the linker component of the water-soluble intermediate react with the spacer component. That is to say that the second water-soluble intermediate still possesses a significant amount of unreacted reactive moieties.

The obtained second water-soluble intermediate precursor may be purified by the methods already discussed in connection with the purification step II), i.e. in connection with the purification of the water-soluble intermediate precursor. As will be evident from the examples provided herein, a suitable method for purifying the obtained second water-soluble intermediate precursor is gel-filtration.

Formation of the Water-Soluble Intermediate Conjugate

In step IIIiii), the signal component is, via reaction with the spacer component, covalently attached to the second water-soluble intermediate precursor, thereby forming a water-soluble intermediate conjugate.

When used herein, the term "signal component" is intended to cover such components which are directly physically detectable or which are precursors for such physically detectable components. In other words, the signal component should function as a label or a marker which can be readily measured by some physical technique known in art, e.g. by means of optical methods, such as spectrophotometry, fluorescence, luminescence, phosphorescence or other methods such as those described in e.g. "Instrumental Methods of Chemical Analysis" G. W. Ewing, 5th Ed., McGraw-Hill Book Company, New York, 1988. Alternatively, the signal component may—as indicated above—be a precursor for a such physically detectable component. A typical example of a such precursor is an enzyme which upon action on a suitable substrate is capable of generating species, preferably coloured species, which can be detected by one or more of the physical methods mentioned above.

In light of the discussion given above, it will be clear to the skilled person that the signal component may be selected from substances such as dyes; fluorescent, luminescent, phosphorescent and other light-emitting substances; metal-chelating substances, including iminodiacetic acid, ethylenediaminetetraacetic acid (EDTA), diethylene triaminepentaacetic acid (DTPA) and desferrioxamine B; substances labelled with a radioactive isotope; substances labelled with a heavy atom; and mixtures thereof.

To give some further examples, fluorescent substances may be selected from, e.g., fluorescein (suitably as fluorescein isothiocyanate, FITC), fluoresceinamine, 1-naphthol, 2-naphthol, eosin, erythrosin, morin, o-phenylenediamine, rhodamine and 8-anilino-1-naphthalenesulfonic acid. Radioactive isotopes of relevance may be selected, for example, among isotopes of hydrogen (i.e. tritium, $^{3}H$), carbon (such as $^{14}C$), phosphorus (such as $^{32}P$), sulfur (such as $^{35}S$), iodine (such as $^{131}I$), bismuth (such as $^{212}Bi$), yttrium (such as $^{90}Y$), technetium (such as $^{99m}Tc$), palladium (such as $^{109}Pd$) and samarium (such as $^{153}Sm$). Heavy atoms of relevance may be selected, for example, among Mn, Fe, Co, Ni, Cu, Zn, Ga, In, Ag, Au, Hg, I, Bi, Y, La, Ce, Eu and Gd. Gold (Au) is a particularly useful heavy atom in many cases.

Signal components which are considered of particular interest are the dyes. In the present context the term "dye" is intended to mean any spectrophotometrically detectable dye molecule or derivative thereof. Preferred dyes to be incorporated in the conjugates prepared by the methods according to the invention are derived from visual dyes, phosphorescent dyes, fluorescent dyes, laser dyes, infrared dyes and lanthanide chelates. Dyes which are particular interesting are visual dyes, including soluble visual dyes, such as solvent dyes, pigments, vat dyes, sulphur dyes, mordant dyes, leucovat dyes and species such as fluorescein, rhodamine and derivatives thereof (such as sulphorhodamine, rhodamine-hydride and rhodamine hydrazide), as well as oxazine dyes, cyanine dyes and azol dyes. Specific examples of suitable dyes are, for example, Texas Red hydrazine, Congo Red, Trypan Blue, Lissamine Blue, Remazol Black, Remazol Brilliant Red, Rhodamine B Isothiocyanate, Cy5-Osu mono functional reactive dye, Reactive Orange 16, Uniblue A, etc.

The above-mentioned dyes, which are useful as signal components for the purposes of the present invention, are all well-known in the art and it will be clear to the skilled person that other dyes can be used as signal components for the purposes of the present invention. Other examples of dyes to be used as signal components are e.g. such dyes as mentioned in "Dyeing and Chemical Technology of Textile Fibers", Trotman, 34th Ed., C. Griffin & Co., London and "The Chemistry of Synthetic Dyes", Vankataramon (Ed.), Academic Press, New York, 1979, the disclosures of which are incorporated herein by reference.

Preferably, the signal component should be capable of reacting with a protein, such as BSA and/or, for alternative embodiments described below, capable of reacting with an unreacted reactive moiety of a linker component). Furthermore, the signal component, upon reacting or binding to the spacer, should preferably not confer any undesirable properties of the resulting water-soluble intermediate conjugate, i.e. the signal component should preferably not promote any uncontrollable non-specific binding nor inhibit the activity of the targeting components (e.g. antibodies) bound to the conjugate. Furthermore, the signal component should preferably not reduce the water solubility of the conjugate significantly.

Depending on the size of the starting dextran, the type of signal component used, and particularly depending on the "load" of the spacer, the "load" of the signal component will obviously vary. As stated earlier, each spacer is able to accommodate several signal components. In preferred embodiments, the number of signal components per spacer component ranges from 1 to 100, expressed in moles of each component. Particularly interesting are the embodiments where the molar ratio ranges from 2 to 80, notably 2 to 75.

As stated earlier, only a small fraction of the reactive moieties of the linking component of the second water-soluble intermediate reacts with the signal component in the formation of the water-soluble intermediate conjugate. Depending on the signal component, the spacer component, and on the linker component, after reacting the signal component, and relative to the amount of unreacted reactive linking component available in the second water-soluble intermediate precursor), from 50 to 100% of the unreacted reactive moieties of the linker component, preferably 60–100%, particularly 70–100%, such as ranging from 80–100% and notably 90–100% remain unreacted (N.B. as compared to the second water-soluble intermediate precursor).

Depending on the particular dye, the conjugate prepared by the method of the invention absorbs or emits photons in the visible range, in the UV range or in the near infrared range, preferably in the visible range. Use of a visual dye such as rhodamine will cause the conjugate of the invention to absorb photons in the visible region (e.g. blue), resulting in the transmission of the complementary wavelength of colour (e.g. red) to an observer. Alternatively, the use of a fluorescent dye will (when radiated) cause the conjugate of the invention to emit photons at a specific wavelength due to the return of electrons to the ground state.

Step IIIiii) of the method of the invention, wherein the water-soluble intermediate conjugate is formed, is conveniently carried out in aqueous solution at a pH above 7, such as above 8, in particular in a range from about 8 to about 11, such as in the range from about 8.5 to 10.5. Depending on the actual signal component employed, the aqueous reaction mixture may contain from 0–60% v/v of an organic co-solvent. Thus, in order to dissolve rather hydrophobic signal component (such as certain dye molecules) it may be necessary to add various amounts of a water-miscible organic co-solvent, such as dimethylsulfoxide (DMSO), ethanol, dimethylformamide (DMF), etc. to the aqueous reaction mixture in order to ensure a sufficient solubility of the employed signal component. In order to avoid denaturation of the previously coupled spacer components (which are typically polypeptides or proteins) the concentration of organic co-solvent in the reaction mixture should preferably be as low as possible.

In a similar way as described above in connection with the steps concerning the formation of the water-soluble intermediate precursor and the formation of the second water-soluble intermediate precursor, it will also in this step be sufficient to carry out the reaction at a temperature in the range from 0–60° C., such as in the range from 20–40° C., e.g. about 30° C.

As will be apparent from the working examples provided herein, the reaction time may be varied within wide limits. Thus the reaction time may depend on, e.g., the "load" of spacer component on the carrier component as well as the usual reaction parameters, such as pH, the temperature, and the nature and concentration of the reactants. In general, however, the reaction time will be in the range of from 1 to 48 hours. Preferably, the reaction time should be as low as possible, i.e. in the range of from 1 to 24 hours, in particular in the range of from 1 to 12 hours, such as in the range of from 1 to 5 hours.

In a similar way as described above, the obtained intermediate conjugate may be purified by a number of different techniques known to the skilled person. Further, the obtained intermediate conjugate may be isolated in a solid form by means of, for example, freeze drying or evaporation of the solvent. In case of the latter, the evaporation is typically carried out under reduced pressure, e.g. by means of a (evacuated) desiccator. The obtained intermediate conjugate may be characterised in various ways. If, for example, the employed signal component is a visual dye, its absorbance can be read and the intermediate conjugate (and hence the efficiency of the coupling step IIIiii)) may, for example, be expressed as the number of Extinction Units (EU) present in the intermediate conjugate per mg of spacer component such as described in Example 4A, herein. The skilled person will, of course, be able to characterise the obtained intermediate conjugate in a number of other ways.

It should be noted that in the method of the invention discussed so far, the spacer component is coupled, via the linking group, to the carrier component after which the signal component is attached to the spacer component. Thus, the spacer component is already attached to the carrier component (via the linking group) when the signal component (such as a dye) is coupled to the spacer component.

Alternatives to the Formation of the Water-Soluble Intermediate Conjugate

As stated earlier, and as will be understood from the examples provided herein, the method is also suitable for the preparation of water-soluble cross-linked conjugates wherein the signal component is covalently attached to the linking component, which in turn is attached to the carrier component, i.e. no protein or polypeptide spacer component is incorporated in the conjugate (vide infra).

In such cases the signal component may, of course, in addition to the signal components mentioned above, also be selected from substances such as proteins, including ferritin, phycoerythrins, phycocyanins and phycobilins; enzymes, including horseradish peroxidase, alkaline phosphatase, glucose oxidases, galactosidases and ureases; and mixtures thereof.

As will be obvious to the skilled person, the signal component may also be covalently attached to the spacer component prior to coupling of the spacer component to the carrier component (via the linking group).

In one preferred embodiment, under certain conditions, only a fraction of the reactive moieties of the linking component of the water-soluble intermediate reacts with the signal component. Depending on the linker component, after reacting the signal component, from 1 to 99% of the unreacted reactive moieties of the linker component, preferably 1–89%, particularly 1–69%, such as ranging from 1 to 59% and notably 1 to 49% remain unreacted. That is to say that in preferred embodiments, from 50 to 99% of the reactive moieties reacted with the signal component.

Accordingly, in another interesting embodiment, the water-soluble intermediate conjugate may be prepared by a method comprising:

I) reacting at least one water-soluble carrier component with more than one linking component in an aqueous solution at a pH above 7, so as to form an aqueous solution containing a water-soluble intermediate precursor comprising water-soluble moieties of the carrier component having covalently attached thereto reactive moieties derived from the linking component;

II) optionally subjecting the water-soluble intermediate precursor to a purification step;

III) reacting the optionally purified water-soluble intermediate precursor, via reaction of said reactive moieties, with at least one spacer component to which at least one signal component has been covalently attached, in an aqueous solution at a pH above 7, so as to form a water-soluble intermediate conjugate, the conditions being such that only a fraction of the reactive moieties reacts with the spacer component to which at least one signal component has been covalently attached; and IV) optionally subjecting the water-soluble intermediate conjugate obtained in step II) to a purification step.

The purification/isolation process may be by methods already discussed in connection with the optional purification of the water-soluble intermediate precursor.

Formation of the Water-Soluble Cross-Linked Conjugate

Turning now to a more detailed discussion of the precipitation step, it will be understood by the skilled person the "key step" in the method of the invention is step a), wherein the primary targeting component is attached to the intermediate conjugate, the reaction conditions being such that a reversible precipitate is formed.

In the present context, the term "reversible precipitate" is intended to mean that the precipitate formed is capable of being re-dissolved upon dilution with water at 25° C. The term "primary targeting component", as used herein, is intended to designate molecules, especially molecules of biological origin, which are capable of selectively binding to, or selectively reacting with, a complementary molecule or a complementary structural region of a material of biological origin. Examples of relevant primary targeting components are, for example: antigens; haptens; monoclonal and polyclonal antibodies; gene probes; natural and synthetic oligo- and polynucleotides; natural and synthetic mono-oligo- and polysaccharides; lectins; avidin; streptavidin; biotin; growth factors; hormones; receptor molecules; protein A and protein G; and mixtures thereof.

Examples of primary targeting components which are considered to be of particular interest for the purpose of the present invention are e.g. anti human Chorionic Gonadotropin (anti hCG), Rabbit anti human CRP, streptavidin, avidin, anti HIV, anti hepatitis C, anti Chlamydia, anti herpes, anti thyroid stimulating hormone (anti TSH), anti Listeria, and anti salmonella.

Examples of relevant primary targeting components, which are hormones, are steroid hormones (e.g. estrogen, progesterone or cortisone), amino acid hormones (e.g. thyroxine) and peptide and protein hormones (e.g. vasopressin, bombesin, gastrin or insulin). EP 0 594 772 B1 mentions at page 12, lines 20–38, that the effectiveness, when attaching molecular species (such as antibodies) to a carrier (such as dextran) may be increased by taking advantage of the so-called "salting out" effect, and it is stated that a suitable concentration will be a concentration corresponding to an ionic strength in the range of from 0.5–5. The examples disclosed in EP 0 594 772 B1 demonstrate that a positive effect with respect to the amount of various species coupled to the carrier was in fact obtained if the salt concentration was increased to a certain level. However, when the salt concentration was increased to about 1 M an irreversible precipitate was formed.

As already mentioned, the present inventors have now surprisingly found that by further increasing the concentration of lyotropic salt in the reaction mixture, a reversible precipitate is formed which contains "large" conjugates which: i) are believed to be extensively a cross-linked, ii) are water-soluble, and iii) have a high sensitivity (due to a "high" load of targeting component and/or a "high" load of signal component) when used in various assays, such as in the lateral flow devices disclosed herein (vide infra). The advantages of the water-soluble cross-linked conjugates, which may be obtained by the methods described herein, will be discussed in details below.

Without being bound by a specific theory it is presently believed that the presence of salt in the reaction mixture causes the activity coefficient of the intermediate conjugate to increase, thereby decreasing the solubility of the intermediate conjugate. In a similar way, the activity coefficient of the primary targeting component (e.g. an antibody) will increase, thereby decreasing the solubility of the primary targeting component. Thus, one hypothesis may be that when the intermediate conjugate as well as the primary targeting component are precipitated (probably together with some co-precipitated water) the two reactants are brought very close together and thereby increasing the probability that a chemical reaction takes place, i.e. increasing the probability that the primary targeting component reacts with the previously unreacted reactive moieties of the linking component. It should be emphasised, however, that the exact mechanism has not presently been solved in detail and, in principle, the extensive cross-linking/attachment of primary targeting component may occur in solution after which the cross-linked conjugate precipitates, or the reaction may take place as the precipitation occurs, or the reaction may occur after the precipitation has taken place (as discussed above). It should be emphasised, however, that irrespective of the actual mechanism by which the cross-linking/attachment of primary targeting component takes place, it can be concluded that the reversible precipitation obtained when using the methods according to the present invention does not—contrary to the teaching disclosed in EP 0 594 772 B1—lead to conjugates having such properties that irreversible precipitation occurs.

Without being limited to a specific theory, it is presently believed that the cross-links established in connection with the precipitation step is constituted, at least to some extent, by the bi-functional linking components, i.e. the first reactive moiety of the linking component is covalently attached to a reactive functionality on a first moiety of a carrier component and the second reactive moiety of the linking component is covalently attached to a reactive functionality on a second moiety of a carrier component. As an illustrative example, the establishment of a cross-link between to dextran carrier components using DVS as linking component may, for example, be as follows:

It is contemplated, however, that cross-linking of the individual carrier components in the precipitation step may be facilitated by the primary targeting component and, accordingly, a cross-link between e.g. two dextran carrier components where e.g. DVS is used as the linking component, may, for example, have the following structure:

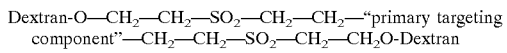

or

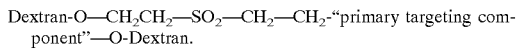

Probably, more than one primary targeting component is incorporated in some of the cross-links and it is contemplated that the primary targeting component may react with a third or even with a fourth linking component thereby establishing cross-links between more than two moieties of carrier components. In fact, the primary targeting component may, at least in principle, react with as many linking components as it possesses reactive sites.

The degree of cross-linking is believed to be directly related to the amount of unreacted reactive moieties of the linker component available to react during the "salting-out" process. The amount of unreacted reactive moieties remaining after the spacer coupling (formation of the second water-soluble intermediate precursor) in preferred embodiments ranges from 50 to 99%, and whereupon subsequent coupling of the signal component (formation of the water-soluble intermediate conjugate), the amount of unreacted reactive moieties, in preferred embodiments, remains unchanged in ranging from 50 to 99%, the amount of reactive moieties available for cross-linking and thus potential for a high degree of cross-linking is great. Clearly, the more extensive the cross-linking (potentially via one or more linkers, between two dextrans, through a spacer or through a primary target) the greater the molecular weight of the conjugate. Obviously, the degree of cross-linking is also related to the method employed for the reversible precipitation step.

The precipitation step a) in the method of the invention is conveniently carried out in an aqueous solution at a pH in the range of 6–11, preferably in the range of 6–10, e.g. in the range of 8–10, in particular in the range of 8–9.

With respect to the reaction time and reaction temperature these parameter may be varied depending on the concentration and/or the nature of the reactants employed. It has been found by the present inventors, however, that a suitable reaction temperature is typically in the range from 2–30° C., such as in the range from 4–16° C., preferably in the range from 4–10° C., in particular at 4–6° C.

The reaction time may be varied between 1 to 36 hours, usually between 6 to 24 hours, e.g. between 15 to 21 hours, such as about 18 hours.

In interesting embodiments of the invention, the initial molar ratio in the solution (i.e. before any precipitation occurs) between the intermediate conjugate and the primary targeting component is in the range from 1:1 to 1:50, such as in the range from 1:1 to 1:25, e.g. in the range from 1:1 to 1:10, preferably in the range from 1:1 to 1:5, in particular in the range from 1:2.5 to 1:5.

The reversible precipitation is preferably performed by salting-out which is conveniently obtained by means of adding lyotropic salts to the reaction mixture. Examples of suitable lyotropic salts are, for example, sulphates, phosphates, citrates or tartrates of lithium, sodium, calcium, potassium or ammonium, or mixtures thereof. Further examples of lyotropic salts are given in "Purification Tools for Monoclonal antibodies", Gagnon, P., Validated Biosystems, 1996, hereby incorporated by reference.

In presently preferred embodiments of the salting-out process, the lyotropic salts calcium phosphate and ammonium sulfate have been particularly effective.

The concentration of the lyotropic salt should be sufficient to ensure that the reversible precipitation process yields a cross-linked conjugate. The concentration of the salt required to effectuate the desirable effect is dependent on the nature of both the cation and anion of the lyotropic salt. As stated earlier, salt concentrations of up to 1 M resulted in the formation of an irreversible precipitate (EP 0 594 772 B1) and did not effectuate the desirable effect. However, salt concentrations greater than 1 M, such as ranging from 1.25 to 3 M, yield the desired cross-linked conjugates. As stated the salt concentration for a particular reversible precipitation will vary according to the choice of the salt used. Moreover, the salt concentration for a particular reversible precipitation will vary according to the load and nature of each of the components. The load and choice of the linker component, the spacer component and signal component will affect the precise salt concentration (of a particular choice of salt). In preferred embodiments, the lyotropic salt concentrations range from 1.25 to 2.75 M, such as at least 1.25 M, or at least 1.5 M, or at least 1.75 M, or at least 2 M, or at least 2.2.5 M, or at least 2.5 M, or at least 2.75 M.

The lyotropic salt should be present in a concentration which is sufficient to ensure that a reversible precipitate is formed, i.e. the concentration of lyotropic salt, namely calcium phosphate or ammonium sulfate, is preferably in the range 1.25 to 2.75 preferably in the range 1.75 to 2.50 M.

Although, as explained above, the salt precipitation step very efficiently couples primary targeting components, any remaining free "dangling" groups derived from the linking component may be deactivated by adding deactivating species of low molecular weight to the aqueous solution containing the reversible precipitate. Examples of suitable deactivating species may be, for example, ethanolamine, mercaptoethanol, or certain amino acids such as cysteine, glycine, alanine or valine.

Following the reversible salt precipitation step, the (reversibly) precipitated conjugates are re-dissolved in an aqueous medium, preferably water. The conjugates obtained according to the methods disclosed herein should be well-soluble in an aqueous medium, such as water, at room temperature and should preferably have a water solubility of at least 0.1, preferably at least 1, such as at least 10, more preferably at least 50, such as at least 100, in particular at least 200 mg of dry conjugate per ml of water at 25° C.

Obviously, and as will be clear to the skilled person, the obtained water-soluble cross-linked conjugate may be further purified and/or isolated in a solid form by means of, for example, freeze drying. The purification/isolation process may be by methods already discussed in connection with the optional purification of the water-soluble intermediate precursor.

Although the precipitation step preferably is carried out by means of addition of lyotropic salt to the reaction mixture it is envisaged that the step, wherein cross-linking/attachment of primary targeting component occurs, may be carried out by means of other techniques than salt precipitation. Thus, one example of an alternative to the above-mentioned salt precipitation is to carry out the reaction in a frozen aqueous solution, i.e. at a temperature in the range from about −20° C. to 0° C. In such frozen solutions small "pockets" of water will occur, wherein the reactants will be present in a very high concentration, thereby increasing the probability that a chemical reaction takes place, i.e. increasing the probability that the primary targeting component reacts with the previously unreacted reactive moieties of the linking component. Still other examples of methods which are contemplated to be useful in the method of the invention include, for example, solvent precipitation, i.e. addition of water-miscible organic solvents to the aqueous reaction mixture; polymer precipitation, i.e. addition of one or more inert polymers to the aqueous reaction mixture; various concentration techniques, such as evaporation, preferably under reduced pressure, etc. The common feature for all the above-mentioned techniques is the enhancement of the proximity of the reactants, thereby increasing the probability that the primary targeting component reacts with the previously unreacted reactive moieties of the linking component.

In embodiments wherein the water-soluble cross-linked conjugate is purified by freeze-drying and wherein any remaining unreacted reactive moieties of the linker component have not been deactivated (using a deactivating species), the level of cross-linking may be augmented by the freeze-drying process. Given that the above stated hypothesis regarding the mechanism by which the cross-linked conjugate is formed is founded on the proximity of the reactants, freeze-drying may simulate, to some extent, in one or more aspects, the salting-out process. Thus, in this embodiment, the level of cross-linking and hence the mean molecular weight may increase compared to that prior the purification process. Conversely, in another embodiment, the unreacted reactive moieties of the linker component are deactivated by said methods prior to the optional purification process.

As already indicated, the main importance of the water-soluble cross-linked conjugates prepared by the methods disclosed herein is presently seen in connection with their use in lateral flow devices, which will be discussed in details below. Therefore, the present inventors have provided a suitable lateral flow device assay which enables the skilled person to select effective and preferred water-soluble cross-linked conjugates prepared by the methods according to the invention. Thus, Example 7A discloses a test for the sensitivity of water-soluble cross-linked conjugates prepared by the methods disclosed herein. It should be noted that the test, when used exactly as described herein, is only suitable for conjugates, wherein the signal component is a visual dye and the primary targeting component is Rabbit anti Human CRP. However, the skilled person will know how to expand the test to encompass other signal components and, more important, other primary targeting components.

As will be acknowledged by the skilled person and as will be apparent from the working examples provided herein, the methods disclosed herein does not necessarily produce "one single type" of conjugate but rather conjugates having a certain molecular weight distribution. From the above-mentioned test it is possible to assess whether the obtained water-soluble cross-linked conjugate is found suitable for the purpose or if further purification/fractionation is desirable. It has been found by the present inventors that in a very interesting embodiment of the invention, the water-soluble cross-linked conjugates obtained in the precipitation step a) is further purified/fractionated by means of gel-filtration. Thus, water-soluble cross-linked conjugates which are very suitable for the use in, for example, lateral flow device systems are such conjugates which, after being re-dissolved in an aqueous medium, are eluted in the void volume when subjected to gel-filtration using, for example, the gel material Sephacryl™ HR S-500 or Sephacryl™ HR S-1000 (using the conditions specified in the working examples disclosed herein).

As indicated previously, the water-soluble cross-linked conjugates are "large" compared to known conjugates. As will be understood by the skilled person, and as mentioned above, the conjugates prepared by the methods disclosed herein will not give rise to a conjugate of a single uniform weight, but rather the obtained conjugates will have a certain molecular weight distribution. Several possible methods, which will be known to the skilled person, may be employed in the determination of different kinds of the average molecular weight of such heterogeneous conjugates. It is envisaged, however, that very suitable methods are, for example, analytical ultracentrifugation and, in particular, light scattering techniques. Thus, in interesting embodiments of the present invention the conjugates obtained by the methods disclosed herein have a mass average molecular weight of at least $10^6$, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $2\times10^7$, at least $3\times10^7$, at least $4\times10^7$, at least $5\times10^7$, at least $6\times10^7$, at least $7\times10^7$, at least $8\times10^7$, at least $9\times10^7$, at least $10^8$, at least $2\times10^8$, at least $3\times10^8$, at least $4\times10^8$, at least $5\times10^8$, at least $6\times10^8$, at least $7\times10^8$, at least $8\times10^8$, at least $9\times10^8$, at least $10^9$, at least $2\times10^9$, at least $3\times10^9$, at least $4\times10^9$, at least $5\times10^9$, at least $6\times10^9$, at least $7\times10^9$, at least $8\times10^9$, at least $9\times10^9$, at least $10^{10}$, at least $2\times10^{10}$, at least $3\times10^{10}$, at least $4\times10^{10}$, at least $5\times10^{10}$, at least $6\times10^{10}$, at least $7\times10^{10}$, at least $8\times10^{10}$, at least $9\times10^{10}$, at least $10^{11}$, at least $2\times10^{11}$, at least $3\times10^{11}$, at least $4\times10^{11}$, at least $5\times10^{11}$, at least $6\times10^{11}$, at least $7\times10^{11}$, at least $8\times10^{11}$, at least $9\times10^{11}$, at least $10^{12}$, at least $2\times10^{12}$, at least $3\times10^{12}$, at least $4\times10^{12}$, at least $5\times10^{12}$, at least $6\times10^{12}$, at least $7\times10^{12}$, at least $8\times10^{12}$, at least $9\times10^{12}$, or at least $10^{13}$ g/mol. Although it is preferred that the conjugates are as large as possible it should be understood that the conjugates should preferably not be larger than the pore size of the solid support material (e.g. nitrocellulose) used in the lateral flow devices as the conjugates should be able to flow in said pores. In a particular interesting embodiment of the present invention the conjugates obtained by the methods disclosed herein have a mass average molecular weight in the range from about $10^6$ to about $10^{10}$ Da, preferably in range $10^6$ to about $10^8$ Da such as in the range from about $10^6$ to about $10^8$ Da.

When using the mass average molecular weight the individual conjugates are weighted according to their mass fractions, m/m, in the sample. Thus, in the present context, the term "mass average molecular weight" is defined with reference to the formula II below:

$$<M> = (1/m)\Sigma_i m_i M_i \tag{II}$$

wherein <M> is the mass average molecular weight, m is the total mass of the sample (i.e. the total mass of the conjugates), and $m_i$ is the total mass of molecules (i.e. conjugates) having a molecular weight of $M_i$.

The gel-filtration profiles (FIGS. 3a–3f) clearly show that the molecular weights of the conjugates prepared in high ionic strength (3a, c, e) are higher than the conjugates prepared in low ionic strength (3b, d, f). Thus an important feature of the present invention lies in that the conjugates prepared by the method of invention are notably different than those prepared to water-soluble polymer-based conjugates prepared by the method described in EP 0 594 772 B1. Structural differences (the degree and nature of the cross-linking) deriving from the method of invention, act in part, along with molecular weight differences and other features to confer activity not previously described for water-soluble polymer-based conjugates.

As mentioned previously in connection with the definition of the term "signal component" the methods disclosed herein are also suitable for the preparation of water-soluble cross-linked conjugates, wherein no spacer component is present, i.e. the signal component, such as an enzyme or a dye molecule, is directly attached, via the linking component, to the carrier component (as described in *Alternatives to the Formation of the Water-Soluble Intermediate Conjugate*).

Thus, in another aspect the present invention relates to a method for the preparation of a water-soluble cross-linked conjugate comprising moieties of at least one carrier component, moieties of more than one linking component, moieties of at least one signal component and moieties of at least one primary targeting component, the signal component being covalently attached, via the linking component, to the carrier component, said method comprising:

a) reacting a water-soluble intermediate conjugate comprising moieties of at least one carrier component, moieties of more than one linking component, moieties of at least one signal component, the signal component being covalently attached, via the linking component, to the carrier component, via reaction of unreacted reactive moieties derived from the linking component, with at least one primary targeting component in an aqueous solution, the conditions being such that a reversible precipitate is formed;

b) re-dissolving the reversible precipitate comprising the water-soluble cross-linked conjugate in an aqueous medium; and c) optionally subjecting the water-soluble cross-linked conjugate to a purification step.

In a similar way, the water-soluble intermediate conjugate, used for the preparation of the water-soluble cross-linked conjugate as described above, may be prepared by a method comprising:

I) reacting at least one water-soluble carrier component with more than one linking component in an aqueous solution at a pH above 7, so as to form an aqueous solution containing a water-soluble intermediate precursor comprising water-soluble moieties of the carrier component having covalently attached thereto reactive moieties derived from the linking component;

II) optionally subjecting the water-soluble intermediate precursor to a purification step;

III) reacting the optionally purified water-soluble intermediate precursor, via reaction of said reactive moieties, with at least one signal component in an aqueous solution at a pH above 7, so as to form a water-soluble intermediate conjugate, the conditions being such that only a fraction of the reactive moieties reacts with the signal component; and IV) optionally subjecting the water-soluble intermediate conjugate obtained in step II) to a purification step.

As it appears, the formation of the water-soluble intermediate conjugate in step III) is the step which differs from the previous discussed methods for preparation of the water-soluble intermediate conjugate. In general, step III) above may be carried out under very similar conditions as described previously for the attachment of signal components to the spacer components. Thus, step III) of the method disclosed above, wherein the water-soluble intermediate conjugate is formed, is conveniently carried out in aqueous solution at a pH above 7, such as in the range from about 8 to 12, preferably in the range from about 9 to 12, in particular in the range from 10 to 12 or in the range from 11 to 12. Depending on the actual signal component employed, the aqueous reaction mixture may contain from 0–60% v/v of an organic co-solvent. Thus, in order to dissolve rather hydrophobic signal component (such as certain dye molecules) it may be necessary to add various amounts of a water-miscible organic co-solvent, such as dimethylsulfoxide (DMSO), ethanol, dimethylformamide (DMF), etc. to the aqueous reaction mixture in order to ensure a sufficient solubility of the employed signal component. It will usually be sufficient to carry out the reaction at a temperature in the range from 0–60° C., such as in the range from 15–40° C., e.g. in the range from 20–25° C.

In general the reaction time will be in the range of from 1 to 48 hours. Preferably, however, the reaction time should be as low as possible, i.e. in the range of from 1 to 24 hours, in particular in the range of from 1 to 12 hours, such as in the range of from 1 to 5 hours.

In a particularly preferred embodiment, the use of a dextran with a peak molecular weight of 500,000, with the use of the linking component DVS within activation degree of 20–30%, the use of the spacer component BSA, the use of the signal component Rhodamine B Isothiocyanate and the use of the either the primary targeting components streptavidin or a monoclonal or polyclonal antibody are the components present in the key reversible precipitation step.

As discussed previously the "key step" in the methods described herein is step a) wherein the primary targeting component is attached to the intermediate conjugate, the reaction being such that a reversible precipitate is formed. Usually, the most expensive reagent to be used for the preparation of the conjugates described herein is the primary targeting component (such as an antibody or an antigen) and, at the same time, the reversible salt precipitation step is one of the most time-consuming steps in the preparation of the conjugates. Furthermore, as the primary targeting will vary depending on the actual target component to be detected a very interesting aspect of the present invention relates to a test kit comprising the water-soluble intermediate conjugate (preferably in the form of a solid) provided with instructions for carrying out the reversible salt precipitation step, the subsequent re-dissolving of the reversible precipitate and the final purification of the thereby formed water-soluble cross-linked conjugate (e.g. by means of gel-filtration). Various modifications of the kit, such as including sets of primary targeting components which are often used in diagnosis/analysis within, for example, the food industry or at hospitals, are also within the scope of the present invention. The kit may, of course, also be provided with instructions for the use of the prepared conjugates in a lateral flow device as described herein.

Formation of the Water-Soluble Cross-Linked Conjugate Complex

In another interesting aspect, the present invention relates to a method for the preparation of a water-soluble cross-linked conjugate complex comprising a conjugate prepared according to any of the methods disclosed herein, a ligand and a secondary targeting component, the ligand being covalently bound to the secondary targeting component, and the ligand being bound to the primary targeting component of the conjugate by means of non-covalent bonds, said method comprising:

I) preparing a water-soluble conjugate according to the methods disclosed herein;

II) reacting the optionally purified water-soluble cross-linked conjugate with a ligand, said ligand being covalently bound to a secondary targeting component, in an aqueous solution;

III) terminating the reaction; and

IV) optionally subjection the water-soluble cross-linked conjugate complex to a purification step.

In the present context the term "secondary targeting component" designates molecules, especially molecules of biological origin, capable of selectively binding to, or selectively reacting with, a complementary molecule or a complementary structural region of a material of biological origin. Thus, the secondary targeting component may be selected from the same class of molecules as mentioned above in connection with the definition of the "term primary targeting component", i.e. examples of interesting secondary targeting components are, for example: antigens; haptens; monoclonal and polyclonal antibodies; gene probes; natural and synthetic oligo- and polynucleotides; natural and synthetic mono- oligo- and polysaccharides; lectins; avidin; streptavidin; biotin; growth factors; hormones; receptor molecules; protein A and protein G; and mixtures thereof. In a particular preferred embodiment of the invention the secondary targeting component is anti hCG.

When used herein, the term "ligand" is intended to mean a molecule having a high affinity for the actual employed primary targeting component, thereby securing a thermodynamically stable non-covalent bond between the ligand and the primary targeting component present in the water-soluble cross-linked conjugate. Thus, in a preferred embodiment of the invention the ligand/primary targeting component are chosen so that the association constant between the ligand and the primary targeting component of the conjugate is at least $10^6$, preferably at least $10^8$, such as at least $10^{10}$, more preferably at least $10^{11}$, such as at least $10^{12}$, in particular at least $10^{13}$, such as at least $10^{14}$, e.g. at least $10^{15}$ l/mol.

As indicated above, the choice of ligand will, of course, be dependent upon the actual primary targeting component employed. Specific examples of suitable ligands are, for example, biotin, anti dinitrophenol or anti dioxygenin, in particular biotin.

In a very interesting embodiment of the invention the ligand/primary targeting component employed is the "biotin/streptavidin system" or the "biotin/avidin system", i.e. the ligand is biotin and the primary targeting component is streptavidin or avidin. As mentioned above, the ligand employed should be covalently bound to a secondary targeting component and, as will be known to the skilled person, biotinylated compounds, such as biotinylated antibodies, are readily available as they can be prepared, for example, as described in Kendall et al. *Journal of Immunological Methods* (1993), 56, 329–339. Thus, by preparing the water-soluble cross-linked conjugates by the methods disclosed herein, using streptavidin or avidin as the primary targeting component, one would obtain a useful "template" onto which any biotinylated secondary targeting component of interest may be attached. It should be understood, however, that any "hapten/antibody systems" may be useful as ligand/primary targeting component provided that the association constant between the employed antibody and the employed hapten fulfils the requirements set forth above.

The reaction step II) mentioned above is usually carried out at room temperature after which the reaction may be terminated [step III)] for example by altering the pH of the reaction mixture and/or by addition of excess free ligand, such as biotin.

As will be understood by the skilled person, the water-soluble cross linked conjugate complexes may be purified by the same methods as mentioned previously in connection with the purification of the water-soluble cross-linked conjugates. In addition hereto, it should be noted that the conjugate complexes may, of course, be isolated in a solid form in a similar way as discussed previously in connection with the conjugates.

As the water-soluble cross-linked conjugates and the water-soluble cross-linked conjugate complexes represent a novel class of compounds another aspect of the present invention relates to a water-soluble cross-linked conjugate comprising moieties of at least one carrier component, moieties of more than one linking component, moieties of at least one spacer component, moieties of at least one signal component and moieties of at least one primary targeting component, the signal component being covalently attached to the spacer component and the spacer component being covalently attached, via the linking component, to the carrier component, wherein the signal component is selected from the group consisting of dyes, proteins (including ferritin, phycoerythrins, phycocyanins and phycobilins), enzymes (including horseradish peroxidase, alkaline phosphatase, glucose oxidases, galactosidases and ureases), fluorescent, luminescent, phosphorescent and other light-emitting substances, metal-chelating substances (including iminodiacetic acid, ethylenediaminetetraacetic acid (EDTA), diethylene triaminepentaacetic acid (DTPA) and desferrioxamine B), substances labelled with a radioactive isotope, substances labelled with a heavy atom, and mixtures thereof;

and the spacer component is selected from the group consisting of proteins and polypeptides.

A still further aspect of the present invention relates to a water-soluble cross-linked conjugate complex comprising a water-soluble cross-linked conjugate as defined herein, a ligand and a secondary targeting component, the ligand being covalently bound to the secondary targeting component, and the ligand being bound to the primary targeting component of the conjugate by means of non-covalent bonds.

As will be understood, details and particulars concerning the properties and constituents of the water-soluble cross-linked conjugates as well as the water-soluble cross-linked conjugate complexes of the invention will be the same as, or analogous to, the details and particulars concerning the properties and constituents of the water-soluble cross-linked conjugates as well as the water-soluble cross-linked conjugate complexes discussed in connection with the method aspects above. This means that wherever appropriate, the statements made in connection with the method aspects apply *mutatis mutandis* to the conjugates and conjugate complexes as such.

Devices and Uses of Conjugates and Complexes

The present invention also relates to a lateral flow device for determining the presence or absence of at least one target component in a liquid sample, said lateral flow device comprising:

I) a test strip comprising an application part, a deposit part and a detection part and being arranged in such a way that the liquid sample can flow from the application part through the deposit part to the detection part;

II) a dry deposit, located in the deposit part of the test strip, of at least one conjugate as defined herein, or a dry deposit of at least one conjugate complex as defined herein, or a mixture thereof; and III) at least one targeting component capable of selectively binding to, or selectively reacting with, one or more target components present in the liquid sample, the targeting component being immobilised on the detection part of the test strip.

In another interesting aspect, the present invention relates to a method for determining the presence or absence of at least one target component in a liquid sample, said method comprising:

I) adding the liquid sample to the application part of the lateral flow device as defined herein;

II) optionally adding a washing buffer to the application part of the lateral flow device;

III) allowing sufficient time for the applied liquid, and where appropriate the washing buffer, to flow from the application part through the deposit part to the detection part;

IV) detecting the presence or absence of a signal in the detection part.

The conjugate and/or the conjugate complex of the invention is supported (as a dry deposit) on the deposit part of the test strip in such a manner that when wetted, the conjugate and/or the conjugate complex is capable of being transported (in a dissolved state) by capillary forces to the detection part of the test strip.

The targeting component which is supported on the detection part of the test strip is supported in a manner such that the targeting component remains immobile and, consequently, cannot be transported by means of capillary forces. Thus, the targeting component may be supported on the test strip, e.g. by means of adsorption, covalent coupling, etc. Procedures for immobilising targeting components, such as antibodies and antigens, on a support material are generally known in the art.

In one embodiment of the invention, the so-called "sandwich" technique, in all its variations as is known by the person skilled in the art, is employed for the test analysis.

As will be understood by the skilled person the so-called "application" part of the test strip, i.e. the part of the test strip which is to be wetted by the sample containing the target component (i.e. the analyte) to be detected, may be identical to the deposit part. Thus, in an interesting embodiment of the invention the sample containing the target component to be detected is applied directly to the part of the test strip comprising the conjugate and/or the conjugate complex.

The test strip is one which is capable of absorbing the target component from the sample applied, and which, when wetted provides for a flow of target component by capillary attraction from the application part through the deposit part (thereby dissolving the dry deposit of conjugate and/or conjugate complex which is then bound to, and transported with, the target component) to the detection part.

The employed strip is made of a material which is capable of supporting the conjugates and/or the conjugate complexes of the invention as well as targeting components such as e.g. antibodies and/or antigens. Examples of suitable materials from which the test strip can be made are e.g. glass fibre, cellulose, nylon, cross-linked dextran, various chromatographic papers, cellulose esters such as nitrocellulose, etc. Presently, the most preferred material is nitrocellulose.

Although referred to as a "strip", wherein the various parts are arranged in the same plane in a manner such that the liquid comprising the target component can flow by capillary attraction from the application part, through the deposit part, to the detection part, the support material may, of course, have any shape or form as long as the requirements with respect to the various parts and flowability are fulfilled.

The liquid comprising the target component to be detected will most often (but not necessarily) be of biological origin such as a blood sample, a serum sample, a plasma sample, a urine sample, a semen sample, or mixtures thereof.

The lateral flow device described herein is capable of detecting small amounts of a variety of target components such as antigens; haptens; monoclonal and polyclonal antibodies; gene probes; natural and synthetic oligo- and polynucleotides; natural and synthetic mono- oligo- and polysaccharides; growth factors; hormones; receptor molecules; as well as mixtures thereof. Specific examples of target components are, for example, hCG, Rabbit human CRP, HIV, hepatitis C, Chlamydia, herpes, thyroid stimulating hormone (TSH), Listeria, Salmonella, and mixtures thereof.

In a particular preferred embodiment of the invention the signal component of the employed water-soluble cross-linked conjugate and/or conjugate complex is a dye which may be directly detectable by the naked eye. Consequently, when such conjugates/conjugate complexes are employed in the lateral flow device disclosed herein it will be possible to visually determine the presence or absence of target component in the applied liquid sample. However, another interesting embodiment of the invention comprises the use of conjugates/conjugate complexes as described herein, wherein the signal component is such a signal component that when applied in the lateral flow device disclosed herein, the signal may be detectable by the naked eye after addition of a reagent to the detection part.

As discussed previously, the conjugates of the present invention are significantly "larger" compared to the conjugates disclosed in the prior art. Although it may be difficult to established the exact structure of the conjugates according to the invention, it is presently believed that extensive cross-linking has taken place which in turn is responsible for the size (and thereby the mass average molecular weight) of the conjugates. As will be apparent from the working examples discloses herein, it appears to be a general rule that the higher molecular weight, the better performance (i.e. the higher sensitivity) is obtained when tested in the "Standard Lateral Flow Performance test" described in Example 7A, herein.

It should be noted that the lateral flow device disclosed in EP 0 291 194 A1 is an example of a suitable lateral flow device, wherein the water-soluble cross-linked conjugates and/or conjugate complexes of the present invention may be incorporated.

In still further aspects, the present invention also relates to the use a water-soluble cross-linked conjugate, as defined herein, and to the use a water-soluble cross-linked conjugate complex, as defined herein, in immunochemical assay techniques, including enzymatic immunoassays (EIA) such as ELISA, radioimmunoassays (RIA), nephelometric and turbidimeric immunoassays, immunohistochemical procedures, cytochemical procedures, flow cytometry, in situ hybridisation techniques, membrane hybridisation techniques, including Southern and Northern blotting, biosensors, lateral flow devices, or methods based on lectin/carbohydrate interactions.

Gel-filtration UV-absorption profile (Example 5A "Solution B", gel-filtration performed on Sephacryl™ S-300) for a sample obtained after coupling of Rabbit anti human CRP to DVS-activated "Dex-BSA-Rhodamine" conjugates in high ionic strength (1.75 M potassium phosphate buffer). The main peak, (1), contains the water-soluble cross-linked "Dex-BSA-Rhodamine/a-CRP" conjugate. On the horizontal axis each mark represents 2 ml. The marks on the vertical axis indicate arbitrary absorption units at 280 nm. The figure shows that free, unbound antibody, peak (2), can be separated from the conjugate.

Figure 2:
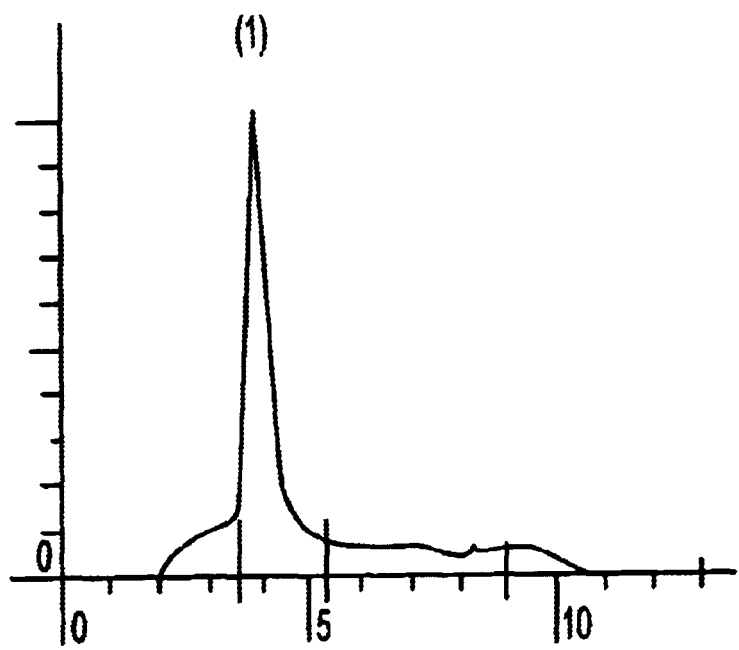

FIG. 2: Characterisation c. Dex-BSA-Rhodamine/a-CRP conjugate

Gel-filtration UV-absorption profile (Example 5A "Solution B", gel-filtration performed on Sephacryl™ S-500) for a sample obtained after coupling of Rabbit anti human CRP to DVS-activated "Dex-BSA-Rhodamine" conjugates in high ionic strength (1.75 M potassium phosphate buffer). The main fraction, (1), contains the water-soluble cross-linked "Dex-BSA-Rhodamine/a-CRP" conjugate. On the horizontal axis each mark represents 2 ml. The marks on the vertical axis indicate arbitrary absorption units at 280 nm. The figure shows that the conjugate has a high and defined molecular weight giving an early eluting and sharp peak.

FIGS. 3a–3f: Characterisation of Conjugates Precipitated in High and Low Ionic Strengths.

Figure 3A:
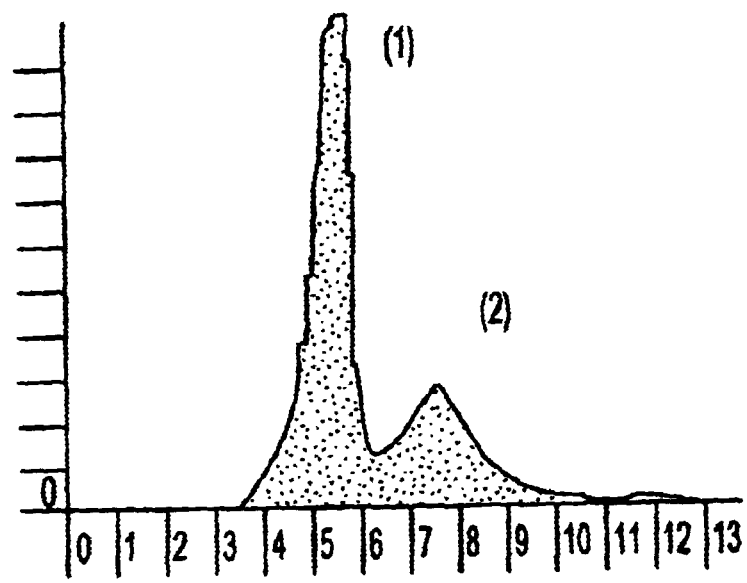
Figure 3B:
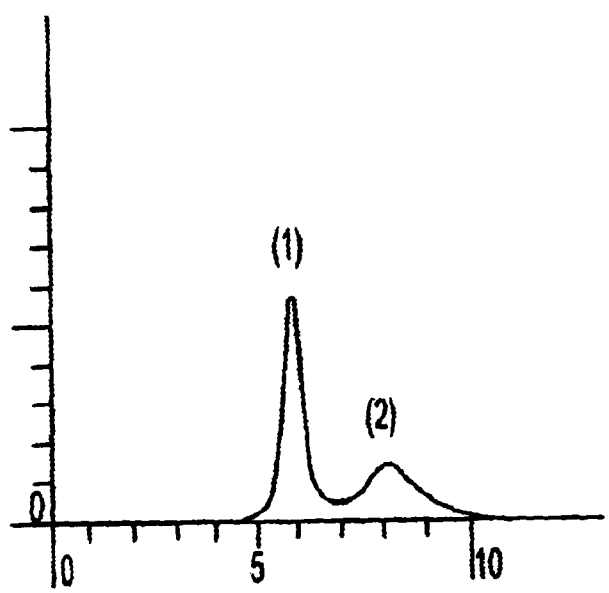
Figure 3C:
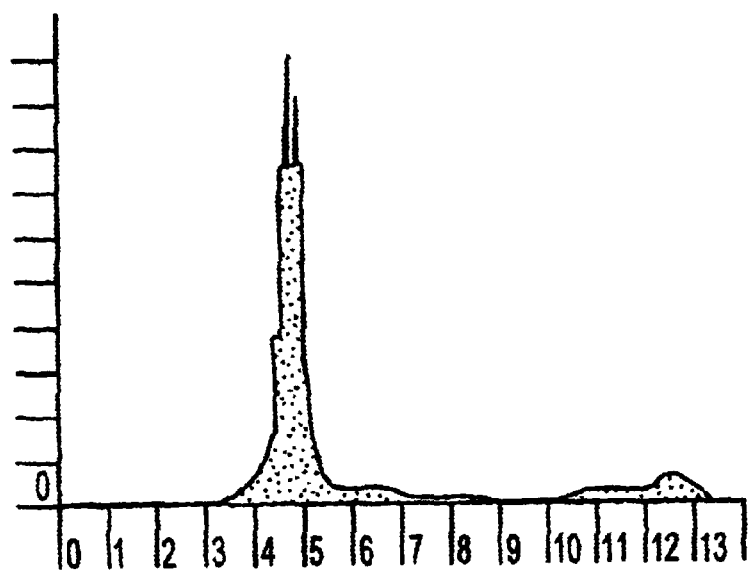
Figure 3D:
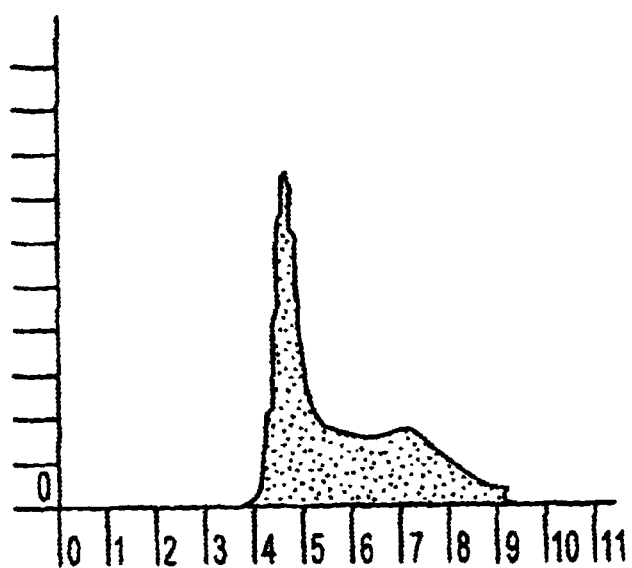
Figure 3E:
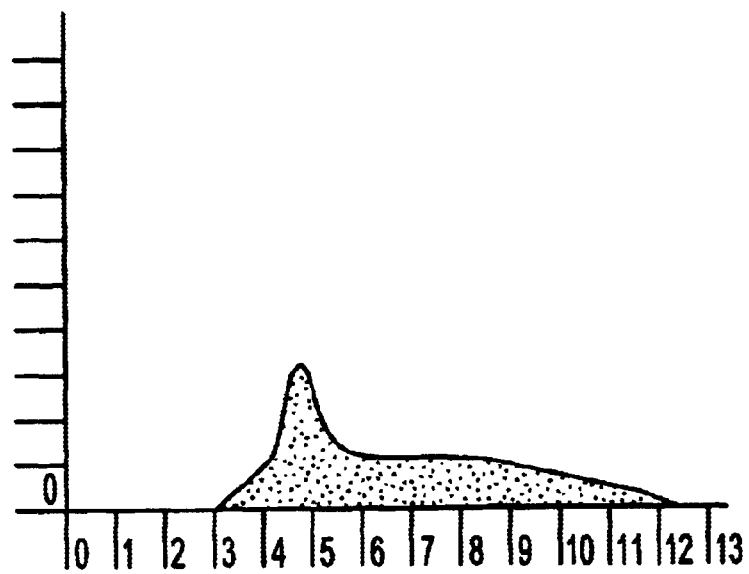
Figure 3F:
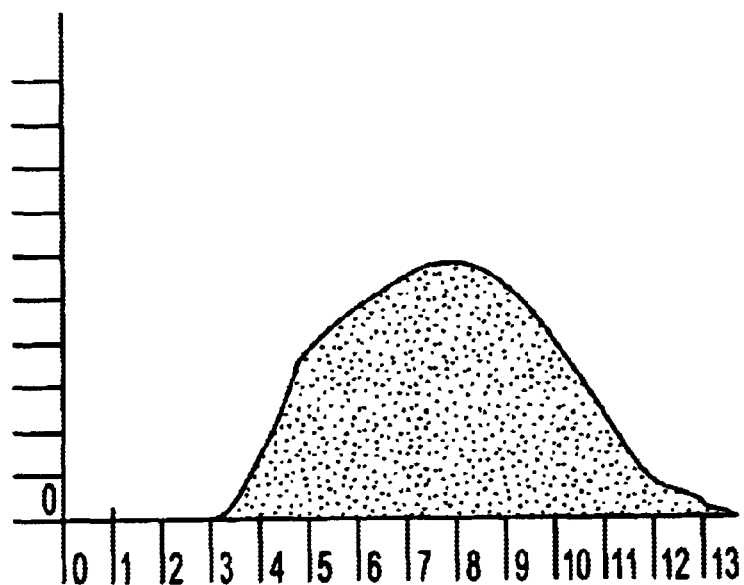

Gel-filtration UV-absorption profiles (FIGS. 3a–b: characterisation profiles of gel-filtration performed on Sephacryl™ HR S-300; FIGS. 3c–d: characterisation profiles of gel-filtration performed on Sephacryl™ HR S-500; FIGS. 3e–f: characterisation profiles of gel-filtration performed on Sephacryl™ HR S-1000) for samples obtained after coupling of Rabbit anti human CRP to DVS-activated "Dex-BSA-Rhodamine" conjugates in high ionic strength (2.2 M potassium phosphate buffer) and low ionic strength (0.1 M potassium phosphate buffer).

FIGS. 3a, 3c, 3e depict conjugates prepared in high ionic strength whereas FIGS. 3b, 3d, 3f depict conjugates prepared in low ionic strength. Label (1) indicates the conjugate whereas label (2) indicates free uncoupled antibody. On the horizontal axis each mark represents 2 ml. The marks on the vertical axis indicate arbitrary absorption units at 280 nm.

The gel-filtration profiles clearly show that the molecular weights of the conjugates prepared in high-ionic strength are higher than the conjugates prepared in low ionic strength.

Figure 4A:
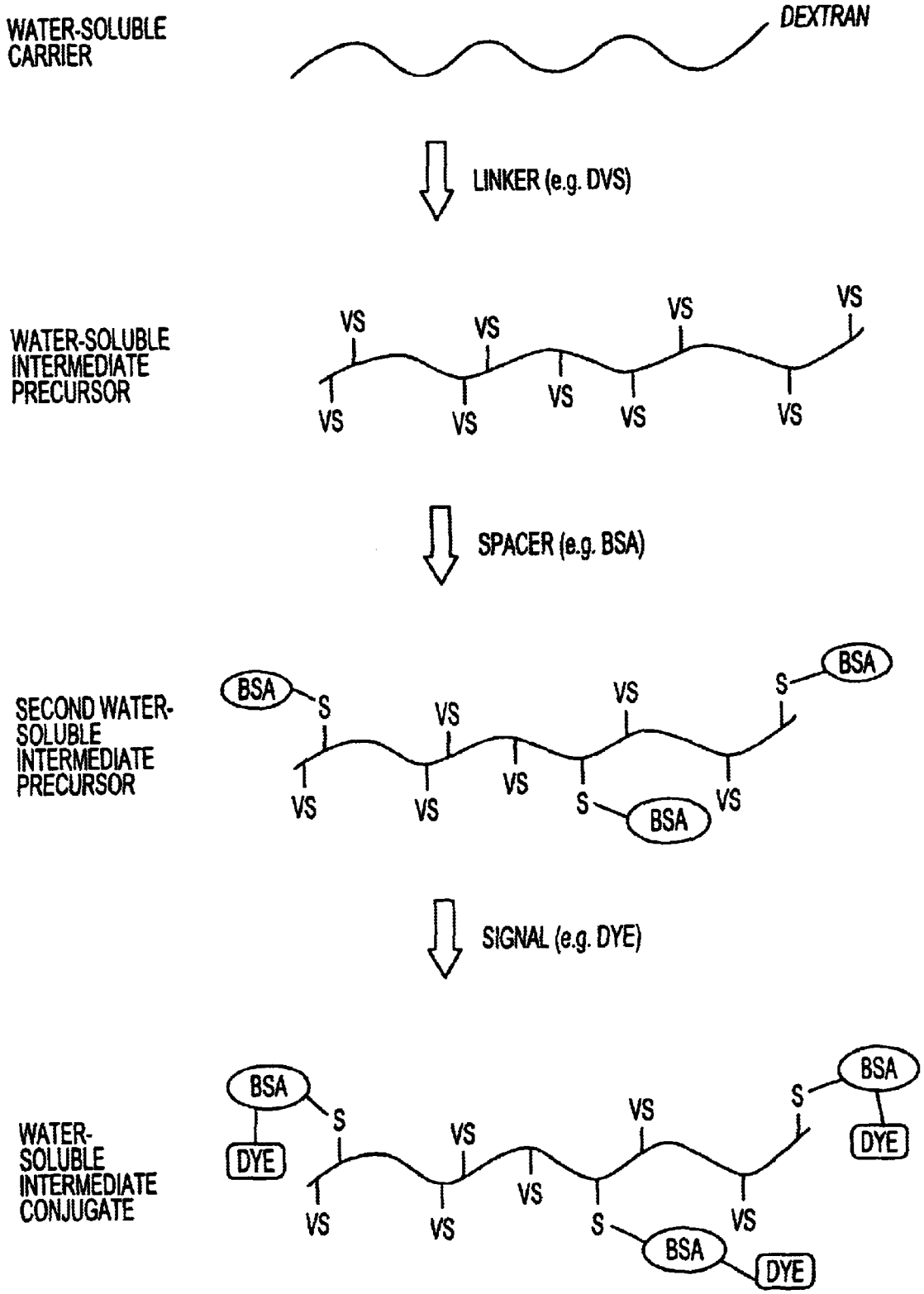
Figure 4B:
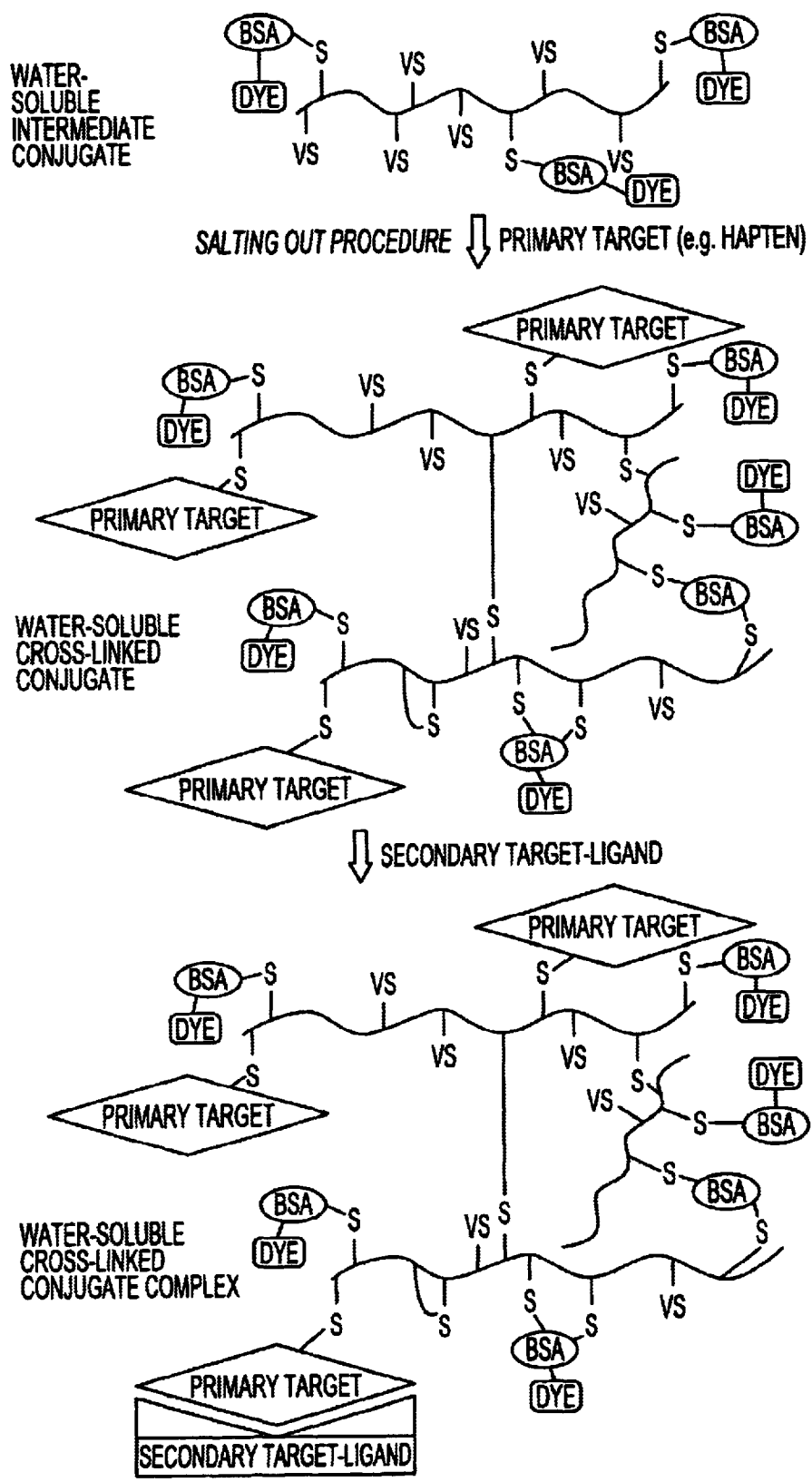

FIG. 4: Outline of the Process for the Preparation of the Water-Soluble Cross-Linked Conjugate Complex.

A schematic representation of one embodiment of the preparation of components and precursors alluded to in the description is depicted in FIG. 4. The Figure is merely to be used for the purpose of clarity as it represents anecdotal examples of one embodiment in order to assist the reader follow the general outline of the procedure described in the method The invention is further illustrated by the working examples described in the following.

EXPERIMENTAL

EXAMPLE 1

Formation of the Water-Soluble Intermediate Precursor

EXAMPLE 1A

DVS activation of dextran having peak MW of 500,000 and 2,000,000

Five separate solutions (A, B, C, D and E) containing the same amount of dextran (obtained from Pharmacia, Sweden), different concentrations of DVS and 0.25 mg of sodium borohydride/ml were prepared in 0.25 M dipotassium hydrogen phosphate/sodium hydroxide (pH 11.5) so as to obtain the following final concentrations:

| Solution | Type of dextran (peak Mw) | Amount of dextran (% w/v) | DVS concentration (% v/v) |
|---|---|---|---|
| A | 500,000 | 1 | 5 |
| B | 500,000 | 1 | 10 |
| C | 2,000,000 | 1 | 3 |
| D | 2,000,000 | 1 | 5 |
| E | 2,000,000 | 1 | 10 |

The dextran was dissolved in water at room temperature (20–25° C.). To the solution was added the same volume of 0.5 M dipotassium hydrogen phosphate/sodium hydroxide (pH 11.5) and 0.25 mg borohydride/ml. Immediately after dissolution of the sodium borohydride the reaction mixture was transferred to a well ventilated hood and DVS (Merck Cat. No. 821215) was added. Gentle stirring was performed with a magnetic stirrer for 30 minutes. After activation the pH of the reaction mixture was adjusted to pH 7 with 25% (v/v) hydrochloric acid.

All five samples were-dialysed thoroughly against water to remove excess reagents. After dialysis the volume of each solution was measured and the final concentration of dextran was calculated.

The content of free, reactive vinyl groups was determined by reaction with a large excess of sodium thiosulphate followed by titration of the resulting hydroxide ions with standardised hydrochloric acid. The reaction of free vinyl groups with thiosulphate takes place according to the following reaction scheme (Porath et al. (1975) *J. Chromatogr.* 103, 49):

(Substrate)—O—CH$_2$—CH$_2$—SO$_2$—CH=CH$_2$ + S$_2$O$_3^{2-}$+H$_2$O→

(Substrate)—O—CH$_2$—CH$_2$—SO$_2$—CH$_2$—CH$_2$—S$_2$O$_3^-$+OH$^-$

The titration results (see the table below) are conveniently expressed as μmoles of vinyl groups per gram of dextran and/or as moles of vinyl groups per mole of dextran. The average number of activated glucose units was calculated in percent of the total amount of glucose units in the dextran molecule (dextran having a peak MW of 500,000 contains in average 2,778 glucose units/dextran molecule and dextran having a peak MW of 2,000,000 contains in average 11,112 glucose units/dextran molecule):

| Solution | μmoles vinyl groups/ g dextran | moles vinyl groups/ mole dextran | % of activated glucose units/ dextran molecule |
|---|---|---|---|
| A | 1,425 | 713 | 26% |
| B | 1,857 | 930 | 33% |
| C | 554 | 1,154 | 10% |
| D | 1,639 | 3,144 | 28% |
| E | 2,078 | 4,175 | 38% |

EXAMPLE 1B

Epichlorohydrin activation of dextran having peak MW of 500,000

Three separate solutions (A, B and C) containing the same amount of dextran with a peak MW of 500,000 were prepared so as to obtain the following final concentrations:

| Solution | Amount of dextran (% w/v) | Epichlorohydrin (% v/v) | Sodium hydroxide (% w/v) |
|---|---|---|---|
| A | 1 | 6 | 1.6 |
| B | 1 | 12 | 3.3 |
| C | 1 | 19 | 4.3 |

The dextran was dissolved in water at room temperature (20–25° C). Sodium hydroxide was added to the solutions and the mixtures were transferred to a well ventilated hood and Epichlorohydrin (Merck Cat. No. 903296) was added. Gentle stirring was performed with a magnetic stirrer for 5 hours. After activation the pH of the reaction mixture was adjusted to pH 7 with 25% (v/v) hydrochloric acid.

All three samples were dialysed thoroughly against water to remove excess reagents. After dialysis the volume of each solution was measured and the final concentration of dextran was calculated.

The content of free, reactive epoxy groups was determined by reaction with a large excess of sodium thiosulphate followed by titration of the resulting hydroxide ions with standardised hydrochloric acid as described in Example 1A. The results obtained were:

| Solution | μmoles epoxy groups/ g dextran | moles epoxy groups/ mole dextran | % activated glucose units/ dextran molecule |
|---|---|---|---|
| A | 323 | 161 | 6% |
| B | 808 | 403 | 15% |
| C | 802 | 400 | 14% |

For the given examples, it can be derived that both DVS and EPCH work well as activating reagents on high and low molecular weight dextrans.

EXAMPLE 2

Formation of the Second Water-Soluble Intermediate Precursor

EXAMPLE 2A

Coupling of Bovine serum albumin (BSA) to DVS-activated dextrans having peak MW of 500,000 and 2,000,000

Five solutions (A, B, C, D and E) of DVS-activated dextran were coupled with BSA (Boehringer Mannheim Cat.

No.100 350). The procedure for coupling BSA to the DVS-activated dextran was as follows:

Solution A: 60 mg of DVS-activated dextran (peak MW of 500,000. Prepared as described for "Solution A" in Example 1A) and 200 mg BSA were dissolved in dipotassium hydrogen phosphate/sodium hydroxide buffer, pH 10.4.

Solution B: 30 mg of DVS-activated dextran (peak MW of 500,000. Prepared as described for "Solution A" in Example 1A) and 200 mg BSA were dissolved in dipotassium hydrogen phosphate/sodium hydroxide buffer, pH 10.4.

Solution C: 152 mg of DVS-activated dextran (peak MW of 2,000,000. Prepared as described for "Solution C" in Example 1A) and 500 mg BSA were dissolved in dipotassium hydrogen phosphate/sodium hydroxide buffer, pH 10.4.

Solution D: 152 mg of DVS-activated dextran (peak MW of 2,000,000. Prepared as described for "Solution D" in Example 1A) and 500 mg BSA were dissolved in dipotassium hydrogen phosphate/sodium hydroxide buffer, pH 10.4.

Solution E: 152 mg of DVS-activated dextran (peak MW of 2,000,000. Prepared as described for "Solution E" in Example 1A) and 500 mg BSA were dissolved in dipotassium hydrogen phosphate/sodium hydroxide buffer, pH 10.4.

After the BSA has dissolved buffer was added to give the following final concentrations:

17 mg BSA/ml
5.2 mg DVS-activated dextran/ml
10 mM dipotassium hydrogen phosphate/sodium hydroxide buffer, pH 10.4

Coupling was performed at 30° C. for 18 hours after which the reaction was stopped by adjusting the pH of the solutions to pH 6–7 by addition of 1 M hydrochloric acid.

The amount of coupled BSA was determined by gel-filtration on Sephacryl HR S-300 (Pharmacia, Sweden, Cat. No.17-0599-01). All gel-filtrations were performed by means of FPLC (Pharmacia, Sweden) using a Pharmacia column (Cat. No. XK26/40) with a diameter of 2.7 cm and a bed volume of 230 ml Sephacryl HR S-300. The gel-filtration was performed in 100 mM sodium chloride with a flow rate of 3 ml/minute and a maximum sample load of 20 ml. The fractions were monitored using a UV-monitor (Pharmacia, Sweden, Cat. No. 19-2448-01/18-0601-01) and a pen recorder (Pharmacia, Sweden, Cat. No. 19-8004-01).

Separation on Sephacryl HR S-300 resulted in two peaks which were collected in two separate fractions.

When using the gel-filtering technique large molecules above the so-called "exclusion limit" of the gel cannot enter the pores and, consequently, such large molecules are eluted from the column in the so-called "void volume", i.e. the void volume is the volume between the individual beads. Usually, the void volume is about 113 of the total volume of the column.

OD 280 nm was measured for both of the collected fractions and the results obtained were expressed as the number of BSA molecules attached to one molecule of dextran with an average MW corresponding to the peak MW of the dextran. The results obtained are compiled below.

| Solution | Type of dextran (peak MW) | Coupling yield (%) | Moles BSA/mole dextran |
|---|---|---|---|
| A | 500,000 | 66 | 17 |
| B | 500,000 | 41 | 21 |
| C | 2,000,000 | 48 | 48 |
| D | 2,000,000 | 55 | 55 |
| E | 2,000,000 | 54 | 54 |

The above values may be calculated as described below:

The coupling performed with 30 mg dextran (peak MW 500,000) and 200 mg BSA (i.e. the molar ratio in the solution is dextran:BSA=1:25) may be calculated in the following way:

A=OD 280 nm, 1 cm cuvette, peak 1 from Sephacryl S-300;
B=OD 280 nm, 1 cm cuvette, peak 2 from Sephacryl S-300;
C=Volume of peak 1 (in ml);
D=Volume of peak 2 (in ml);
$\epsilon$ (BSA,280 nm,1 cm,1 mg/ml)=0.65;
mg BSA in peak 1=(A×C)0.65=Y mg BSA;
mg BSA in peak 2=(B×D)/0.65=Z mg BSA;
Percent coupled BSA=(Y×100)/(Y+Z);
Coupled moles BSA/mole dextran=(Ratio of dextran:BSA×% coupled BSA)/100;

The first peak (i.e. the peak obtained in the void volume from Sephacryl HR S-300) containing BSA coupled to dextran is hereafter referred to as "Dex-BSA" conjugate.

The "Dex-BSA" conjugates were characterised on Sephacryl HR S-500 (Pharmacia, Sweden, Cat. No 17-0613-01). All gel-filtrations were performed by means of FPLC (Pharmacia, Sweden) using a FPLC column (Cat. No. HR 10/30, Pharmacia, Sweden) with a bed volume of 25 ml Sephacryl HR S-500. The gel-filtration was performed in 100 mM sodium chloride with a flow rate of 1 ml/minute and a maximum sample load (on each run) of 100–500 µl.

Separation on Sephacryl HR S-500 resulted in two partly fused peaks. The first peak (peak one) was eluted after 8 ml in the "void volume" (The void volume of 25 ml Sephacryl HR S-500 is 8 ml).

Characterisation on Sephacryl HR S-500 was expressed as percent "Dex-BSA" conjugate located in the first peak of the profile (hereafter referred to the as "conjugate eluted in the void volume"). By calculation of the size of the fraction, the fraction was measured from start of peak one until mark 5.25 (i.e. 10.5 ml from start of the gel-filtration). The obtained results were:

| Solution | % "Dex-BSA" conjugate eluted in the void volume |
|---|---|
| A | 30 |
| B | 18 |
| C | 41 |
| D | 41 |
| E | 36 |

EXAMPLE 2B

Coupling of Bovine serum albumin (BSA) to Epichlorohydfin-activated dextrans having peak MWof 500,000

Three solutions (A, B and C) of Epichlorohydrin-activated dextran were coupled with BSA (Boehringer Mannheim Cat. No. 100 350). The procedure for coupling BSA to the DVS-activated dextran was as follows:

Solution A: 90 mg of Epichlorohydrin-activated dextran (peak MW of 500,000. Prepared as described for "Solution A" in Example 1B) and 300 mg BSA were dissolved in dipotassium hydrogen phosphate/sodium hydroxide buffer, pH 10.4.

Solution B: 90 mg of Epichlorohydrin-activated dextran (peak MW of 500,000. Prepared as described for "Solution B" in Example 1B) and 300 mg BSA were dissolved in dipotassium hydrogen phosphate/sodium hydroxide buffer, pH 10.4.

Solution C: 90 mg of Epichlorohydrin-activated dextran (peak MW of 500,000. Prepared as described for "Solution C" in Example 1B) and 300 mg BSA were dissolved in dipotassium hydrogen phosphate/sodium hydroxide buffer, pH 10.4.

After the BSA has dissolved buffer was added to give the following final concentrations:
18 mg BSA/ml
5.5 mg Epichlorohydrin-activated dextran/ml
10 mM dipotassium hydrogen phosphate/sodium hydroxide buffer, pH 10.4

Coupling was performed at 30° C. for 18 hours after which the reaction was stopped by adjusting the pH of the solutions to pH 6–7 by addition of 1 M hydrochloric acid.

The amount of coupled BSA was determined by gel-filtration on Sephacryl HR S-300 as described in Example 2A.

The results obtained were:

| Solution | Type of dextran (peak MW) | Coupling yield (%) | Moles BSA/mole dextran |
|---|---|---|---|
| A | 500,000 | 24 | 4 |
| B | 500,000 | 30 | 5 |
| C | 500,000 | 29 | 6 |

The "Dex-BSA" conjugates were then characterised on Sephacryl HR S-500 as described in Example 3A. Separation on Sephacryl resulted in a double peak but no peak of "Dex-BSA" conjugate was observed in the void volume fraction.

From the given examples it can be derived that two different types of dextran activation give satisfactory coupling yields using BSA as the spacer component.

EXAMPLE 3

Formation of the Water-Soluble Intermediate Conjugate

EXAMPLE 3A

Coupling of Rhodamine dye to DVS-activated Dextran-BSA conjugates

Three solutions (A, B and C) of "Dex-BSA" with two different peak MW of dextran (peak MW 500,000 and 2,000,000, respectively) were coupled with Rhodamine B Isothiocyanate (Sigma, Cat. No. R 1755, Rhodamine ITC).

Solution A: "Dex-BSA" of peak MW 500,000 coupled 17 moles BSA/mole dextran as described for "Solution A" in Example 2A.

Solution B: "Dex-BSA" of peak MW 500,000 coupled 17 moles BSA/mole dextran as described for "Solution A" in Example 2A.

Solution C: "Dex-BSA" of peak MW 2,000,000 coupled 48 moles BSA/mole dextran as described for "Solution C" in Example 2A.

Three separate solutions with 20 mg BSA (as "Dex-BSA") and Rhodamine ITC (from a stock solution at 5 mg Rhodamine ITC/ml DMSO) were mixed with buffer to give the following final concentrations:
Solution A: 400 µg Rhodamine ITC/ml and 2 mg BSA/ml
Solution B+C: 200 µg Rhodamine ITC/ml and 2 mg BSA/ml
All three solutions contained 30% DMSO and 0.2 M sodium hydrogen carbonate, pH 8.6.

Coupling was performed at 30° C. for 3 hours after which the solutions were dialysed thoroughly against 10 mM potassium phosphate buffer, pH 7.2, to remove excess reagents.

After dialysis the volume of each solution was measured and the amount of "Dex-BSA" coupled to Rhodamine ITC (hereafter referred to as "Dex-BSA-Rhodamine" conjugate) was calculated. The optical density at 558 nm (1 cm cuvette) was measured for all samples and Extinction Units (EU) were calculated for each sample. The results obtained were:

| Solution | Type of dextran (peak MW) | Moles BSA/mole dextran | EU/mg BSA |
|---|---|---|---|
| A | 500,000 | 17 | 29 |
| B | 500,000 | 17 | 13 |
| C | 2,000,000 | 48 | 11 |

As indicated in the above table, the amount of coupled Rhodamine ITC may be expressed as OD 558 EU/mg BSA. This value may be calculated as follows:
A=Volume of "Dex-BSA-Rhodamine" solution after dialysis
B=mg BSA used in the coupling
Coupled OD 558 EU/mg BSA=(A×OD 558)/B The "Dex-BSA-Rhodamine" conjugates were characterised on Sephacryl HR S-500 (Pharmacia, Sweden, Cat. No.17-0613-01) and Sephacryl S-300 (Pharmacia, Sweden, Cat. No. 17-0599-01).

All gel-filtrations were performed as described in Example 2A for S-500 gel-filtration on a FPLC (Pharmacia, Sweden) in a FPLC column (Pharmacia, Sweden, Cat. No. HR 10/30) with a bed volume of 25 ml Sephacryl HR S-300 or 25 ml Sephacryl HR S-500. The gel-filtrations were performed in 50 mM Tris 0.1 M sodium chloride,1% v/v Tween 20 adjusted to pH 9 with 1 M hydrochloric acid. The flow rate was 1 ml/minute and the load of sample was 100–500 µl (on each run) depending on the concentration of the sample. The results obtained were:

| Solution | % "Dex-BSA-Rhodamine" (S-300) | conjugate eluted in the void volume (S-500) |
|---|---|---|
| A | 69% | 36% |
| B | 52% | 52% |
| C | 31% | 41% |

EXAMPLE 3B

Coupling of Rhodamine dye to EPCH-activated Dextran-BSA conjugates

Three solutions (A, B and C) of "Dex-BSA" with peak MW 500,000 were coupled with Rhodamine B Isothiocyanate (Sigma, Cat. No. R 1755, Rhodamine ITC).

Solution A: "Dex-BSA" of peak MW 500,000 coupled 4 moles BSA/mole dextran as described for"Solution A" in Example 2B.

Solution B: "Dex-BSA" of peak MW 500,000 coupled 5 moles BSA/mole dextran as described for "Solution B" in Example 2B.

Solution C: "Dex-BSA" of peak MW 500,000 coupled 6 moles BSA/mole dextran as described for "Solution C" in Example 2B.

Three separate solutions with 6 mg BSA (as "Dex-BSA") and Rhodamine ITC (from a stock solution at 5 mg Rhodamine ITC/ml DMSO) were mixed with buffer to give the following final concentrations:

200 μg Rhodamine ITC/ml
0.5 mg BSA/ml
30% Dimethylsulfoxide
0.2 M Sodium hydrogen carbonate, pH 8.6

Coupling and subsequent dialysis was performed as described in Example 3A.

After dialysis, the optical density at 558 nm (1 cm cuvette) was measured for all samples and Extinction Units (EU) were calculated for each sample. The results obtained were:

| Solution | Type of dextran (peak MW) | Moles BSA/mole dextran | EU/mg BSA |
|---|---|---|---|
| A | 500,000 | 4 | 25 |
| B | 500,000 | 5 | 24 |
| C | 500,000 | 6 | 25 |

The Dex-BSA-Rhodamine conjugates were characterized on Sephacryl HR S-500 and Sephacryl S-300 as described in Example 4A, the only difference being the eluent which contained 50 mM Tris, 0.1 M sodium chloride, 0.5% v/v Tween-20 adjusted to pH 7.2 with 1 M hydrochloric acid. The results obtained were

| Solution | % "Dex-BSA-Rhodamine" (S-300) | conjugate in the void volume (S-500) |
|---|---|---|
| A | 60% | 13% |
| B | 71% | 17% |
| C | 70% | 17% |

EXAMPLE 3C

Coupling of Cy5 dye to DVS-activated Dextran-BSA conjugates

Two solutions (A and B) of "Dex-BSA" with peak MW 500,000 were coupled with Cy5-OSu mono functional reactive dye (Amersham Pharmacia Biotec UK, Cat. No. PA 15102).

Solution A and B: "Dex-BSA" of peak MW 500,000 coupled 17 moles BSA/mole dextran as described for "Solution A" in Example 2A.

Two separate solutions with BSA (as "Dex-BSA") and Cy5 (from a stock solution at 8 mg Cy5/ml DMSO) were mixed with buffer to give the following final concentrations:

Solution A: 2 mg BSA/ml, 4000 μg Cy5/ml, 50% DMSO, 0.05 M sodium hydrogen carbonate, pH 8.6.

Solution B: 1 mg BSA/ml, 4000 μg Cy5/ml, 50% DMSO, 0.05 M sodium hydrogen carbonate, pH 8.6.

Coupling and subsequent dialysis was performed at described in Example 3A, the only difference being that the reaction time was decreased to 2 hours.

After dialysis, the optical density at 655 nm (1 cm cuvette) was measured for all samples and Extinction Units (EU) were calculated for each sample. The results obtained were:

| Solution | Type of dextran (peak MW) | Moles BSA/mole dextran | EU/mg BSA |
|---|---|---|---|
| A | 500,000 | 17 | 57 |
| B | 500,000 | 17 | 87 |

EXAMPLE 3D

Coupling of Reactive Orange dye to DVS-activated Dextran-BSA conjugates

A solution of "Dex-BSA" with peak MW 500,000 coupled 17 moles BSA/mole dextran as described for "Solution A" in Example 2A was coupled with Reactive Orange 16 (Aldrich, Cat. No.30.650-9).

A solution containing 10 mg BSA (as "Dex-BSA") and Reactive Orange 16 (from a stock solution at 5 mg Reactive Orange 16/ml DMSO) was mixed with buffer to give the following final concentrations:

5 mg BSA/ml
250 μg Reactive Orange 16/ml
5% DMSO
0.4 M potassium phosphate, pH 10.4

Coupling and subsequent dialysis was performed at described in Example 3A, the only difference being that the reaction time was increased to 18 hours.

After dialysis, the optical density at 493 nm (1 cm cuvette) was measured for the sample and Extinction Units (EU) were calculated for the sample. The results obtained were:

| Type of dextran (peak MW) | Moles BSA/mole dextran | EU/mg BSA |
|---|---|---|
| 500,000 | 17 | 1.4 |

The "Dex-BSA-Reactive Orange 16" conjugate was characterised on Sephacryl HR S-500 and Sephacryl HR S-300 as described in Example 3A, the only difference being the eluent which contained 50 mM Tris, 0.1 M sodium chloride, 0.5% v/v Tween-20 adjusted to pH 7.2 with 1 M hydrochloric acid. The results obtained were:

| % "Dex-BSA-Reactive Orange 16" (S-300) | conjugate in the void volume (S-500) |
|---|---|
| 86% | 17.4% |

EXAMPLE 3E

Coupling of Uniblue A dye to DVS-activated Dextran-BSA conjugates

A solution of "Dex-BSA" with peak MW 500,000 coupled 17 moles BSA/mole dextran as described for "Solution A" in Example 2A was coupled with Uniblue A (Sigma, Cat. No. 29.840-9).

A solution containing 10 mg BSA (as "Dex-BSA") and Uniblue A (from a stock solution at 5 mg Uniblue A/ml DMSO) was mixed with buffer to give the following final concentrations:
5 mg BSA/ml
500 µUniblue A/ml
10% DMSO
0.4 M potassium phosphate pH, 10.4

Coupling and subsequent dialysis was performed at described in Example 3A.

After dialysis, the optical density at 595 nm (1 cm cuvette) was measured for the sample and Extinction Units (EU) were calculated for the sample. The results obtained were:

| Type of dextran (peak MW) | Moles BSA/mole dextran | EU/mg BSA |
|---|---|---|
| 500,000 | 17 | 3 |

The "Dex-BSA-Uniblue A" conjugate was characterised on Sephacryl HR S-500 and Sephacryl HR S-300 as described in Example 3A, the only difference being the eluent which contained 50 mM Tris, 0.1 M sodium chloride, 0.5% v/v Tween-20 adjusted to pH 7.2 with 1 M hydrochloric acid. The results obtained were:

| % "Dex-BSA-Uniblue A" (S-300) | conjugate in the void volume (S-500) |
|---|---|
| 78% | 16% |

From the given examples it can be derived that a number of different dyes coupled efficiently to a Dex-BSA intermediate, which had been activated by either DVS or EPCH.

EXAMPLE 4

Formation of the Water-Soluble Intermediate Conjugate

EXAMPLE 4A

Coupling of Rabbit anti Human CRP to DVS-activated "Dex-BSA-Rhodamine" conjugates in high ionic strength Five solutions (A, B, C, D and E) of "Dex-BSA-Rhodamine" conjugates were coupled with the Rabbit anti Human CRP Immunoglobulin fraction (DAKO, Denmark, Cat. No. Q 0329). Solution A and D: "Dex-BSA-Rhodamine" of peak MW 500,000 coupled 29 OD 558 Units/mg BSA as described for "Solution A" in Example 3A.

Solution B, C and E: "Dex-BSA-Rhodamine" of peak MW 500,000 coupled 13 OD 558 Units/mg BSA as described for "Solution B" in Example 3A.

The following solutions containing antibody and "Dex-BSA-Rhodamine" were prepared:

Solution A and B: 0.0016 µmol antibody and 0.000645 µmol dextran (as "dex-BSA-Rhodamine") were mixed with 3.5 M potassium phosphate buffer, pH 8.8, to give the following final concentrations:
1.75 M potassium phosphate buffer
pH 8.6
0.24 mg antibody/ml
Molar ratio in the solution: "dex-BSA-Rhodamine"/Antibody: 1/2.5

Solution C: 0.007742 µmol antibody and 0.001548 µmol dextran (as "dex-BSA-Rhodamine") were mixed with 3.5 M potassium phosphate buffer, pH 8.8, to give the following final concentrations:
2.2 M potassium phosphate buffer
pH 8.6
0.21 mg antibody/ml
Molar ratio in the solution: "dex-BSA-Rhodamine"/Antibody: 1/5

Solution D: 0.003226 µmol antibody and 0.00129 µmol dextran (as "dex-BSA-Rhodamine") were mixed with 3.5 M potassium phosphate buffer, pH 8.8, to give the following final concentrations:
2.2 M potassium phosphate buffer
pH 8.6
0.13 mg antibody/ml
Molar ratio in the solution: "dex-BSA-Rhodamine"/Antibody: 1/2.5

Solution E: 0.0016 µ/mol antibody and 0.000645 µmol dextran (as "dex-BSA-Rhodamine") were mixed with 3.5 M potassium phosphate buffer, pH 8.8, to give the following final concentrations:
2.2 M potassium phosphate buffer
pH 8.6
0.15 mg antibody/ml
Molar ratio in the solution: "dex-BSA-Rhodamine"/Antibody: 1/2.5

After mixing a precipitate was observed in the solution and coupling of the antibody was continued at 46° C. for 18 hours. After coupling, cysteine (Merck, Cat. No. 1.02838) was added to the samples to a final concentration of 0.01 M cysteine. The concentration of phosphate buffer in solution C, D and E was adjusted to 1.75 M by addition of de-ionised water to the solution. All five solutions were the spun for 5 minutes at 10,000 rpm and the supernatants, which were clear and almost colourless, were carefully aspirated with a pipette. The precipitate (pellets) containing free antibody and coupled antibody was dissolved in de-ionised water.

Pellets from solution A and B were dissolved in 400 µl de-ionised water and Tween-20 was added to a final concentration of 1% v/v.

Pellets from solution C were dissolved in 700 µl de-ionised water followed by dialysis for one hour against 50 mM Tris and 0.1 M sodium chloride adjusted to pH 7.2 with 1 M hydrochloric acid. After dialysis Tween-20 was added to a final concentration of 0.5% v/v.

Pellets from solution D and C were dissolved in 500 µl de-ionised water and Tween-20 was added to a final concentration of 0.5% v/v.

Free antibody and "Dex-BSA-Rhodamine"-bound antibody in the samples were separated by gel-filtration on Sephacryl HR S-300 (Pharmacia, Sweden, Cat. No. 17-0599-01). All gel-filtrations were performed on a FPLC (Pharmacia, Sweden) using a Pharmacia column (Cat. No. HR 10/30) with a diameter of 1 cm and a bed volume of 25 ml Sephacryl HR S-300. The gel-filtrations of solutions A and B were performed in 50 mM Tris, 0.1 M sodium chloride, 1% v/v Tween-20 adjusted to pH 9 with 1 M hydrochloric acid. The gel-filtrations of solutions C, D and E were performed in 50 mM Tris, 0.1 M sodium chloride, Tween-20 adjusted to pH 7.2 with 1 M hydrochloric acid (Concentration of Tween 20 for solution C and D: 0.5% v/v. Concentration of Tween-20 for solution E: 0.1% v/v). All gel-filtrations were performed with a flow rate of 1 ml/minute.

Separation on Sephacryl HR S-300 resulted in two peaks. Peak one from Sephacryl HR S-300 containing Rabbit anti Human CRP coupled to "Dex-BSA-Rhodamine ITC" is hereafter referred to as "Dex-BSA-Rhodamine/a-CRP" conjugate.

Figure 1:
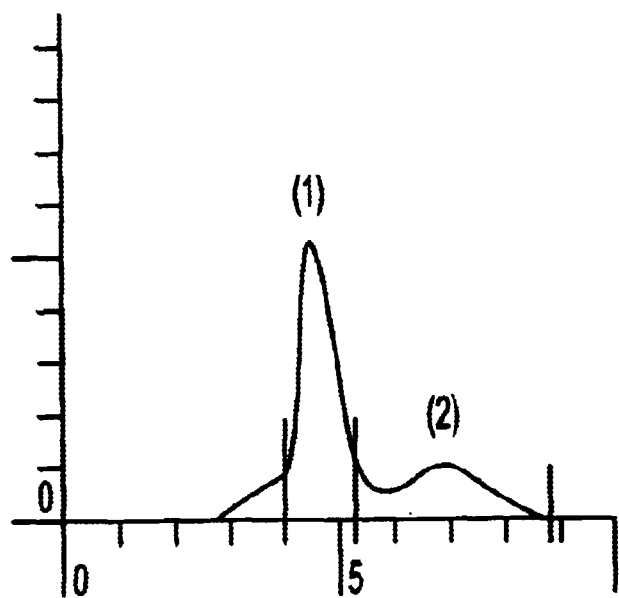
FIG. 1: Purification of Dex-BSA-Rhodamine/a-CRP conjugate

The "Dex-BSA-Rhodamine/a-CRP" conjugate (obtained from "solution B") was collected as one fraction from 8 to 10.5 ml (from mark 4 to 5.25 at the profile shown in FIG. 1)

OD 558 was measured for the "Dex-BSA-Rhodamine/a-CRP" conjugates and the conjugates were then characterised on Sephacryl HR S-500 (Pharmacia, Sweden, Cat. No.17-0613-01). All gel-filtrations were performed by means of FPLC (Pharmacia, Sweden) using a FPLC column (Cat. No. HR 10/30, Pharmacia Sweden) with a bed volume of 25 ml Sephacryl HR S-500. Solutions A and B were gel-filtered in 50 mM Tris, 0.1 M sodium chloride, 1% v/v Tween-20 adjusted to pH 9 with 1 M hydrochloric acid. Solutions C and E were gel-filtered in 50 mM Tris, 0.1 M sodium chloride, Tween-20 adjusted to pH 7.2 with 1 M hydrochloric acid (Concentration of Tween 20 for solution C: 0.5% v/v. Concentration of Tween-20 for solution E: 0.1% v/v). All gel-filtrations were performed with a flow rate of 1 ml/minute.

Separation on Sephacryl HR S-500 ("solution B") resulted in one major peak which was eluted after 7 ml as shown in FIG. 2. However, by gel-filtration of the conjugate from solution C two peaks were collected. Fraction one was collected from 7 to 10.5 ml and fraction two was collected from 10.5 to 18 ml.

The characterisation on Sephacryl HR S-500 was expressed as percent "Dex-BSA-Rhodamine/a-CRP" conjugate located in the first peak of the profile, hereafter referred to as "conjugate eluted in void volume". The size of the fraction was from the start of the peak one until 10.5 ml from the start of the gel-filtration. The results obtained were:

| Solution | OD 558 of peak one obtained after gel-filtration on Sephacryl HR S-300 | % conjugate eluted in the void volume after gel-filtration on Sephacryl HR S-500 |
|---|---|---|
| A | 2.5 | 74% |
| B | 1.4 | 70% |
| C | 2.5 | 54% |
| D | 1.7 | 51% |
| E | 1.1 | 80% |

EXAMPLE 4B

Coupling of Rabbit anti Human CRP to EPCH-activated "Dex-BSA-Rhodamine" conjugates in high ionic strength A solution of "Dex-BSA-Rhodamine" conjugate was coupled with the Rabbit anti Human CRP immunoglobulin fraction (DAKO, Denmark, Cat. No. Q 0329).

"Dex-BSA-Rhodamine" of peak MW 500,000 coupled 25 OD 558 Units/mg BSA as described for "Solution C" in Example 3B.

The following solution containing antibody and "Dex-BSA-Rhodamine" was prepared:

0.003226 $\mu$mol antibody and 0.00129 $\mu$mol dextran (as "Dex-BSA-Rhodamine")was mixed with 3.5 M potassium phosphate buffer, pH 8.8, to give the following final concentrations:

2.2 M potassium phosphate buffer
pH 8.6
0.1 mg antibody/ml
Molar ratio in the solution: "Dex-BSA-Rhodamine"/ Antibody: 1/2.5

After mixing a precipitate was observed in the solution and coupling of the antibody was continued at 4–6° C. for 18 hours. After coupling, cysteine (Merck, Cat. No. 1.02838) was added to the samples to a final concentration of 0.01 M cysteine. The concentration of phosphate buffer in the solution was adjusted to 1.75 M by addition of de-ionised water to the solution. The solution was spun for 5 minutes at 10,000 rpm and the supernatant, which was clear and almost colourless, was carefully aspirated with a pipette. The pellets containing free antibody and coupled antibody were dissolved in 500 $\mu$l deionised water and Tween-20 was added to a final concentration of 0.5% w/v.

Free antibody and "Dex-BSA-Rhodamine"-bound antibody in the sample was separated by gel-filtration on Sephacryl HR S-300 in 50 mM Tris, 0.1 M sodium chloride, 0.5% Tween-20 adjusted to pH 7.2 with 1 M hydrochloric acid, and peak one from Sephacryl HR S-300 was characterised on Sephacryl HR S-500 as described in Example 4A. Subsequent separation on Sephacryl HR S-500 (as described in Example 4A) resulted in two overlapping peaks. The first peak, peak one was eluted after 7 ml. The obtained results were:

| OD 558 of peak one obtained after gel-filtration on Sephacryl HR S-300 | % conjugate eluted in the void volume after gel-filtration on Sephacryl HR S-500 |
|---|---|
| 0.45 | 42% |

EXAMPLE 4C

Coupling of anti hCG monoclonal antibody to DVS-activated "Dex-BSA-Rhodamine" conjugates in high ionic strength A solution of "Dex-BSA-Rhodamine" conjugate was coupled with anti hCG monoclonal antibody, Mab (Genzyme MIH, Batch No. M21452). "Dex-BSA-Rhodaminen" of peak MW 500,000 coupled 29 OD 558 Units/mg BSA as described for "Solution A in Example 3A.

The following solution containing antibody and "Dex-BSA-Rhodamine" was prepared:

0.0016 $\mu$mol antibody and 0.00064 $\mu$mol dextran (as "Dex-BSA-Rhodamine")was mixed with 3.5 M potassium phosphate buffer, pH 8.8, to give the following final concentrations:

2.2 M potassium phosphate buffer
pH 8.6
0.06 mg antibody/ml
Molar ratio in the solution: "Dex-BSA-Rhodamine"/ Antibody: 1/2.5

After mixing a precipitate was observed in the solution and coupling of the antibody was continued at 4–6° C. for 18 hours. After coupling, cysteine (Merck, Cat. No. 1.02838) was added to the samples to a final concentration of 0.01 M cysteine. The concentration of phosphate buffer in the solution was adjusted to 1.75 M by addition of de-ionised water to the solution. The solution was spun for 5 minutes at 10,000 rpm and the supernatant, which was clear and almost colourless, was carefully aspirated with a pipette. The pellets containing free antibody and coupled antibody were dissolved in 500 $\mu$l deionised water and Tween-20 was added to a final concentration of 0.5% wv.

Free antibody and "Dex-BSA-Rhodamine"-bound antibody in the sample was separated by gel-filtration on Sephacryl HR S-300 in 50 mM Tris, 0.1 M sodium chloride, 0.5% Tween-20 adjusted to pH 7.2 with 1 M hydrochloric acid, and peak one from Sephacryl HR S-300 was characterised on Sephacryl HR S-500 as described in Example 4A. Subsequent separation on Sephacryl HR S-500 (as described in Example 4A) resulted in two overlapping peaks. The first peak, peak one was eluted after 7 ml. The obtained results were:

| OD 558 of peak one obtained after gel-filtration on Sephacryl HR S-300 | % conjugate eluted in the void volume after gel-filtration on Sephacryl HR S-500 |
|---|---|
| 0.88 | 58% |

EXAMPLE 4D
Coupling of Rabbit anti Human CRP to DVS-activated "Dex-BSA-Reactive Orange 16" conjugates in high ionic strength A solution of "Dex-BSA-Reactive Orange 16" conjugate was coupled with the Rabbit anti Human CRP immunoglobulin fraction (DAKO, Denmark, Cat. No. Q 0329).

"Dex-BSA-Reactive Orange 16" of peak MW 500,000 coupled 1.4 OD 493 Units/mg BSA as described in Example 3D.

The following solution containing antibody and "Dex-BSA-Reactive Orange 16" was prepared:

0.00323 µmol antibody and 0.00129 µmol dextran (as "Dex-BSA-Reactive Orange 16") was mixed with 3.5 M potassium phosphate buffer, pH 8.8, to give the following final concentrations:
2.2 M potassium phosphate buffer
pH 8.6
0.23 mg antibody/ml
Molar ratio in the solution: "Dex-BSA-Reactive Orange 16"/Antibody: 1/2.5

After mixing a precipitate was observed in the solution and coupling of the antibody was continued at 46° C. for 18 hours. After coupling, cysteine (Merck, Cat. No.1.02838) was added to the samples to a final concentration of 0.01 M cysteine. The concentration of phosphate buffer in the solution was adjusted to 1.75 M by addition of de-ionised water to the solution. The solution was spun for 5 minutes at 10,000 rpm and the supernatant, which was clear and almost colourless, was carefully aspirated with a pipette. The pellets containing free antibody and coupled antibody were dissolved in 500 µl deionised water and Tween-20 was added to a final concentration of 0.5% w/v.

Free antibody and "Dex-BSA-Reactive Orange 16"-bound antibody in the sample were separated by gel-filtration on Sephacryl HR S-300 in 50 mM Tris, 0.1 M sodium chloride, 0.5% Tween-20 adjusted to pH 7.2 with 1 M hydrochloric acid, and peak one from Sephacryl HR S-300 was characterised on Sephacryl HR S-500 as described in Example 4A. Subsequent separation on Sephacryl HR S-500 (as described in Example 4A) resulted in two overlapping peaks. The first peak, peak one was eluted after 7 ml. The obtained results were:

| OD 493 of peak one obtained after gel-filtration on Sephacryl HR S-300 | % conjugate eluted in the void volume after gel-filtration on Sephacryl HR S-500 |
|---|---|
| 0.73 | 55% |

EXAMPLE 4E
Coupling of Rabbit anti Human CRP to DVS-activated "Dex-BSA-Uniblue A" conjugates in high ionic strength Two solutions (A and B) of "Dex-BSA-Uniblue A" conjugates were coupled with the Rabbit anti Human CRP Immunoglobulin fraction (DAKO, Denmark, Cat. No. Q 0329).

"Dex-BSA-Uniblue A" of peak MW 500,000 coupled 3 OD 595 Units/mg BSA as described in Example 3E.

The following solutions containing antibody and "Dex-BSA-Uniblue A" were prepared:

Solution A: 0.0015 µmol antibody and 0.0015 µmol dextran (as "dex-BSA-Uniblue A") were mixed with 3.5 M potassium phosphate buffer, pH 8.8, to give the following final concentrations: 2.2 M potassium phosphate buffer
pH 8.6
0.09 mg antibody/ml
Molar ratio in the solution: "dex-BSA-Uniblue A"/Antibody: 1/1

Solution B: 0.0030 µmol antibody and 0.0015 µmol dextran (as "dex-BSA-Uniblue A") were mixed with 3.5 M potassium phosphate buffer, pH 8.8, to give the following final concentrations:
2.2 M potassium phosphate buffer
pH 8.6
0.2 mg antibody/ml
Molar ratio in the solution: "dex-BSA-Uniblue A"/Antibody: 1/2

After mixing a precipitate was observed in the solution and coupling of the antibody was continued at 4–6° C. for 18 hours. After coupling, cysteine (Merck, Cat. No. 1.02838) was added to the samples to a final concentration of 0.01 M cysteine. The concentration of phosphate buffer in the solution was adjusted to 1.75 M by addition of de-ionised water to the solution. Both solutions were spun for 5 minutes at 10,000 rpm and the supernatants, which were clear and almost colourless, were carefully aspirated with a pipette. The pellets containing free antibody and coupled antibody were dissolved in 500 µl deionised water and Tween-20 was added to a final concentration of 0.5% w/v.

Free antibody and "Dex-BSA-Uniblue A"-bound antibody in the sample were separated by gel-filtration on Sephacryl HR S-300 in 50 mM Tris, 0.1 M sodium chloride, 0.5% Tween-20 adjusted to pH 7.2 with 1 M hydrochloric acid, and peak one from Sephacryl HR S-300 was characterised on Sephacryl HR S-500 as described in Example 4A. Subsequent separation on Sephacryl HR S-500 (as described in Example 4A) resulted in two overlapping peaks. The first peak, peak one was eluted after 7 ml. The obtained results were:

| Solution | OD 595 of peak one obtained after gel-filtration on Sephacryl HR S-300 | % conjugate eluted in the void volume after gel-filtration on Sephacryl HR S-500 |
|---|---|---|
| A | 0.86 | 52% |
| B | 0.88 | 48% |

EXAMPLE 4F
Comparison of the coupling of Rabbit anti Human CRP to DVS-activated "Dex-BSA-Rhodamine" conjugates in high and low ionic strength Two solutions (A and B) of "Dex-BSA-Rhodamine" conjugates were coupled with the Rabbit anti Human CRP Immunoglobulin fraction (DAKO, Denmark, Cat. No. Q 0329).

Solution A and B: "Dex-BSA-Rhodamine" of peak MW 500,000 coupled 13 OD 558 Units/mg BSA as described for"Solution B" in Example 3A.

The following solutions containing antibody and "Dex-BSA-Rhodamine" were prepared:

Solution A: 0.01548 μmol antibody and 0.003097 μmol dextran (as "dex-BSA-Rhodamine") were mixed with 3.5 M potassium phosphate buffer, pH 8.8, to give the following final concentrations:
2.2 M potassium phosphate buffer
pH 8.6
0.21 mg antibody/ml
Molar ratio in the solution: "dex-BSA-Rhodamine"/ Antibody: 1/5

Solution B: 0.00645 μmol antibody and 0.00129 μmol dextran (as "dex-BSA-Rhodamine") were mixed with 3.5 M potassium phosphate buffer, pH 8.8, and water to give the following final concentrations:
0.1 M potassium phosphate buffer
pH 8.6
0.54 mg antibody/ml
Molar ratio in the solution: "dex-BSA-Rhodamine"/ Antibody: 1/5

After mixing a precipitate was observed in solution A. Both couplings were continued at 4–6° C. for 18 hours. After coupling, cysteine (Merck, Cat. No. 1.02838) was added to the samples to a final concentration of 0.01 M cysteine. The concentration of phosphate buffer in solution A was adjusted to 1.75 M by addition of de-ionised water to the solution. Solution A was then spun for 5 minutes at 10,000 rpm and the supernatant, which was clear and almost colourless, was carefully aspirated with a pipette. The precipitate (pellets) containing free antibody and coupled antibody was dissolved in 1 ml de-ionised water. The re-dissolved precipitate (obtained from solution A) and solution B (which was a clear liquid without precipitate) were dialysed for one hour against 50 mM Tris, 0.1 M sodium chloride adjusted to pH 7.2 with 1 M hydrochloric acid.

Characterisation by gel-filtration:

Peak one obtained from gel-filtration on Sephacryl HR S-300 was characterised on Sephacryl HR S-500 and Sephacryl HR S-1000 as described in Example 4A.

The obtained profiles from the gel-filtration on Sephacryl HR-300, HR S-500 and HR S-1000 are shown in FIGS. 3a–3f.

EXAMPLE 4G

Coupling of Streptavidin to DVS-activated "Dex-BSA-Rhodamine" conjugates in high ionic strength Five solutions (A, B, C, D and E) of "Dex-BSA-Rhodamine" conjugates were coupled with Streptavidin (KEM-EN-TEC, Denmark, Cat. No. 4610H). All samples coupled 25 OD 558 Units/mg BSA as described for "Solution A" in Example 3B.

The following solutions containing antibody and "Dex-BSA-Rhodaminen" were prepared:

Solution A: 0.00833 μmol Streptavidin and 0.004165 μmol dextran (as "dex-BSA-Rhodamine") were mixed with 3.5 M potassium phosphate buffer, pH 9, to give the following final concentrations:
2.5 M potassium phosphate buffer
pH 9
0.05 mg Streptavidin/ml
Molar ratio in the solution: "dex-BSA-Rhodamine"/ Streptavidin: 1/2

Solution B: 0.00833 μmol Streptavidin and 0.001667 μmol dextran (as"dex-BSA-Rhodamine") were mixed with 3.5 M potassium phosphate buffer, pH 9, to give the following final concentrations:
2.5 M potassium phosphate buffer
pH 9
0.11 mg Streptavidin/ml
Molar ratio in the solution: "dex-BSA-Rhodamine"/ Streptavidin: 1/5

Solution C: 0.00833 μmol Streptavidin and 0.000833 μmol dextran (as "dex-BSA-Rhodamine") were mixed with 3.5 M potassium phosphate buffer, pH 9, to give the following final concentrations:
2.5 M potassium phosphate buffer
pH 9
0.22 mg Streptavidin/ml
Molar ratio in the solution: "dex-BSA-Rhodamine"/ Streptavidin: 1/10

Solution D: 0.00833 μmol Streptavidin and 0.0004165 μmol dextran (as "dex-BSA-Rhodamine") were mixed with 3.5 M potassium phosphate buffer, pH 9, to give the following final concentrations:
2.5 M potassium phosphate buffer
pH 9
0.42 mg Streptavidin/ml
Molar ratio in the solution: "dex-BSA-Rhodamine"/ Streptavidin: 1/20

Solution E: 0.00833 μmol Streptavidin and 0.000208 μmol dextran (as "dex-BSA-Rhodamine") were mixed with 3.5 M potassium phosphate buffer, pH 9, to give the following final concentrations:
2.5 M potassium phosphate buffer
pH 9
0.71 mg Streptavidin/ml
Molar ratio in the solution: "dex-BSA-Rhodamine"/ Streptavidin: 1/40

After mixing a precipitate was observed in the solutions and coupling of Streptavidin was continued at 4–6° C. for 18 hours. After coupling, cysteine (Merck, Cat. No. 1.02838) was added to the samples to a final concentration of 0.01 M cysteine. The concentration of phosphate buffer in all solutions was adjusted to 1.75 M by addition of de-ionised water to the solutions. All five solutions were the spun for 5 minutes at 10,000 rpm and the supernatants, which were clear and almost colourless, were carefully aspirated with a pipette. The precipitate (pellets) containing free Streptavidin and coupled Streptavidin was dissolved in de-ionised water.

The pellets from all the solutions were dissolved in 1 ml de-ionised water. The solutions were dialysed for one hour against 0.1 M sodium chloride and 50 mM Tris adjusted to pH 7.2 with 1 M hydrochloric acid. After dialysis Tween-20 was added to the solutions to a final concentration of 0.1% v/v and solutions were spun for 5 minutes at 10,000 rpm and the supernatants (the sample) were carefully aspirated with a pipette, whereas the rest of the conjugates (pellets) were not used.

Free Streptavidin and "Dex-BSA-Rhodamine"-bound Streptavidin in the samples were separated by gel-filtration on Sephacryl HR S-300 (Pharmacia, Sweden, Cat. No. 17-0599-01). All gel-filtrations were performed on a FPLC (Pharmacia, Sweden) using a Pharmacia column (Cat. No. HR 10/30) with a diameter of 1 cm and a bed volume of 25 ml Sephacryl HR S-300. All gel-filtrations were performed in 50 mM Tris, 0.1 M sodium chloride, 0.1% v/v Tween-20 adjusted to pH 7.2 with 1 M hydrochloric acid using a flow rate of 1 ml/minute.

Separation on Sephacryl HR S-300 resulted in two peaks. Peak one from Sephacryl HR S-300 containing Streptavidin coupled to "Dex-BSA-Rhodamine ITC" is hereafter referred to as "Dex-BSA-Rhodamine/Streptavidin" conjugate.

The "Dex-BSA-Rhodamine/Streptavidin" conjugate was collected as one fraction after 8 ml.

OD 558 was measured for the "Dex-BSA-Rhodamine/Streptavidin" conjugates and the conjugates were then characterised on Sephacryl HR S-500 (Pharmacia, Sweden, Cat. No.17-0613-01). All gel-filtrations were performed by means of FPLC (Pharmacia, Sweden) using a FPLC column (Cat. No. HR 10/30, Pharmacia Sweden) with a bed volume of 25 ml Sephacryl HR S-500. All solutions were gel-filtered in 50 mM Tris, 0.1 M sodium chloride, 0.1% v/v Tween-20 adjusted to pH 7.2 with 1 M hydrochloric acid using a flow rate of 1 ml/minute.

Separation on Sephacryl HR S-500 resulted in one major peak which was eluted after 7 ml.

The characterisation on Sephacryl HR S-500 was expressed as percent "Dex-BSA-Rhodamine/Streptavidin" conjugate located in the first peak of the profile, hereafter referred to as "conjugate eluted in void volume". The results obtained were:

| Solution | OD 558 of peak one obtained after gel-filtration on Sephacryl HR S-300 | % conjugate eluted in the void volume after gel-filtration on Sephacryl HR S-500 |
|---|---|---|
| A | 6 | 77% |
| B | 4 | 75% |
| C | 2.7 | 72% |
| D | 1.6 | 71% |
| E | 0.7 | 65% |

From the given examples it can be derived that a number of different primary targeting components, which are antibodies or specific binding molecules, can be coupled, preferably at high ionic strength, to activated dextrans carrying a spacer component and a dye.

EXAMPLE 5

Alternatives to the Formation of the Water-Soluble Conjugate

EXAMPLE 5A

Coupling of dye to DVS-activated dextran having a peak MW of 2,000,000

Dextran (peak MW of 2,000,000) was activated with DVS as described for "Solution C" in Example 1A (i.e. using 1% (w/v) of dextran and 3% (v/v) of DVS). The activated dextran had a content of 554 μmoles of reactive vinyl groups per gram of dextran. The final concentration of DVS-activated dextran was 8.3 mg activated dextran/ml.

Four separate solutions (A, B, C and D) containing the same concentration of DVS-activated dextran were prepared. Buffer was added so that the final concentration of dipotassium hydrogen phosphate/sodium hydroxide was 0.25 M and the final concentration of sodium chloride was 0.50 M. pH of the solutions was 11.5.

A concentrated solution of dye (Remazol-Black B gran, DE HA 725, Hoechst) was added after filtering through a 0.45 μm filter. The final concentrations of DVS" activated dextran and dye were as follows:

| Solution | Amount of dextran (% w/v) | Amount of dye (% w/v) |
|---|---|---|
| A | 0.4 | 1.0 |
| B | 0.4 | 0.50 |
| C | 0.4 | 0.25 |
| D | 0.4 | 0.13 |

Solution A, B, C and D were incubated at room temperature (20–25° C.) for 3 hours. After coupling the pH of the reaction mixture was adjusted to pH 8 with 1 M hydrochloric acid. All samples were dialysed thoroughly against 50 mM sodium chloride to remove uncoupled dye. After dialysis the volume of each solution was measured and the final concentrations of dextran were calculated.

After dialysis each sample was measured at OD 600 nm (1 cm cuvette) and characterised by the number of OD 600 units coupled/mg dextran. The results of the coupling reactions are compiled below:

| Solution | OD 600 units coupled/mg dextran |
|---|---|
| A | 11 |
| B | 8 |
| C | 4 |
| D | 2 |

The number of OD 600 units coupled/mg dextran was calculated according to the formula:

$$(A \times B)/C = OD\ 600\ \text{units coupled/mg dextran}$$

where A is OD 600 as measured after ended dialysis, B is the volume of the solution obtained after ended dialysis and C is the amount (mg) of DVS-activated dextran used in the experiment.

EXAMPLE 5B

Coupling of dye to DVS-activated dextran having a peak MW of 2,000,000

Dextran (peak MW of 2,000,000) was activated with DVS as described for "Solution C" in Example 1A (i.e. using 1% (w/v) of dextran and 3% (v/v) of DVS). The activated dextran had a content of 554 μmoles of reactive vinyl groups per g dextran. The final concentration of DVS-activated dextran was 8.3 mg activated dextran/ml.

Two separate solutions (A and B) containing the same concentration of DVS-activated dextran were prepared. Buffer was added so that the final concentration of dipotassium hydrogen phosphate/sodium hydroxide was 0.25 M and the final concentration of sodium chloride was 0.50 M. pH of the solutions was 11.5.

A concentrated solution of dye (Remazol Brilliant Red F3B, DE BE 305, Hoechst) was added after filtering through a 0.45 μm filter. The final concentrations of DVS-activated dextran and dye were as follows:

| Solution | Amount of dextran (% w/v) | Amount of dye (% w/v) |
|---|---|---|
| A | 0.4 | 0.50 |
| B | 0.4 | 0.25 |

Solution A and B were incubated at room temperature (20–25° C.) for 4 hours. After coupling the pH of the reaction mixture was adjusted to pH 7 with 1 M hydrochloric acid. All samples were dialysed thoroughly against 50 mM sodium chloride to remove uncoupled dye. After dialysis the volume of each solution was measured and the final concentrations of dextran were calculated.

After dialysis each sample was measured at OD 530 nm (1 cm cuvette) and characterised by the number of OD 530 units coupled/mg dextran. The results of the coupling reactions are compiled below:

| Solution | OD 530 units coupled/mg dextran |
|---|---|
| A | 7 |
| B | 5 |

The number of OD 530 units coupled/mg dextran was calculated as described in Example 5A.

From the given examples it can be derived that two different dyes (black or red) coupled almost the same amount of OD.

EXAMPLE 6

Alternatives to the Formation of Water-Soluble Cross-Linked Conjugate

EXAMPLE 6A

Coupling of Rabbit anti Human CRP to DVS-activated "Dex-Remazol Black" conjugates in high ionic strength.

Five solutions (A, B, C, D and E) of "Dex-Remazol Black" conjugates were coupled with the Rabbit anti Human CRP immunoglobulin fraction (DAKO, Denmark Cat. No. Q 0329).

Solution A and E: "Dex-Remazol Black" of peak MW 2,000,000 coupled 11 OD 600 Units/mg dextran as described for "Solution A" in Example 5A.

Solution B: "Dex-Remazol Black" of peak MW 2,000,000 coupled 8 OD 600 Units/mg dextran as described for "Solution B" in Example 5A Solution C: "Dex-Remazol Black" of peak MW 2,000,000 coupled 4 OD 600 Units/mg dextran as described for "Solution C" in Example 5A.

Solution D: "Dex-Remazol Black" of peak MW 2,000,000 coupled 2 OD 600 Units/mg dextran as described for "Solution D" in Example 5A.

Solution A, B, C and D: 0.003226 $\mu$mol antibody and 0.000645 $\mu$mol dextran (as "Dex-Remazol Black") were mixed with 3.5 M potassium phosphate buffer, pH 8.8, to give the following final concentrations:
1.75 M potassium phosphate buffer
pH 8.6
0.6 mg antibody/ml
Molar ratio in the solution: "Dex-Remazol Black"/ Antibody: 1/5

Solution E: 0.00645 $\mu$mol antibody and 0.00129 $\mu$mol dextran (as "Dex-Remazol Black") were mixed with 3.5 M potassium phosphate buffer, pH 8.8, to give the following final concentrations:
2.2 M potassium phosphate buffer
pH 8.6
0.22 mg antibody/ml
Molar ratio in the solution: "Dex-Remazol Black"/ Antibody: 1/5

After mixing, a precipitate was observed in the solutions and coupling of the antibody was continued at 4–6° C. for 18 hours. After coupling, cysteine (Merck, Cat. No.1.02838) was added to the samples to a final concentration of 0.01 M cysteine. Solutions A, B, C and D were dialysed for one hour against 0.1 M potassium phosphate buffer, pH 9. After dialysis Tween-20 was added to a final concentration of 0.5% v/v.

The concentration of phosphate buffer in solution E was adjusted to 1.75 M by addition of de-ionised water to the solution. The conjugate was spun for 5 minutes at 10,000 rpm and the supernatant was carefully aspirated with a pipette. The precipitate (pellets) was dissolved 1 ml de-ionised water and Tween-20 was added to a final concentration of 0.5% vv.

Free antibody and "Dex-Remazol Black"-bound antibody in the samples were separated by gel-filtration on Sephacryl HR S-300 (Pharmacia, Sweden, Cat. No. 17-0599-01). All gel-filtrations were performed on a FPLC (Pharmacia, Sweden) using a Pharmacia column (Cat. No. HR 10/30) with a diameter of 1 cm and a bed volume of 25 ml Sephacryl HR S-300. For solutions A, B, C and D, the gel-filtration was performed in 0.1 M potassium phosphate buffer, pH 9,0.5% v/v Tween-20. Solution E was gel-filtered in 50 mM Tris, 0.1 M sodium chloride, 0.5% Tween pH adjusted to pH 7.2 with 1 M hydrochloric acid. All gel-filtrations were performed with a flow rate of 1 ml/minute.

Separation on Sephacryl HR S-300 resulted in two peaks. Peak one from Sephacryl HR S-300 containing Rabbit anti Human CRP coupled to "Dex-Remazol Black" is hereafter referred to as "Dex-Remazol Black/a-CRP" conjugate. The "Dex-Remazol Black/a-CRP" conjugate was collected as one fraction after 8 ml.

OD 600 was measured for the "Dex-Remazol Black/a-CRP" conjugates and the conjugates from solution A, B, C and D were then characterised on Sephacryl HR S-500 (Pharmacia, Sweden Cat. No. 17-0613-01). All gel-filtrations were performed by means of FPLC (Pharmacia, Sweden) using a FPLC column (Cat. No. HR10/30, Pharmacia Sweden) with a bed volume of 25 ml Sephacryl HR S-500. The gel-filtrations were performed in 0.1 M potassium phosphate buffer, pH 9, 0.5% v/v Tween-20 and a flow rate of 1 ml/minute.

Separation on Sephacryl HR S-500 resulted in two overlapping peaks. The first peak, peak one, was eluted after 7 ml.

The characterisation on Sephacryl HR S-500 was expressed as percent "Dex-Remazol Black/a-CRP" conjugate located in the first peak of the profile, hereafter referred to as "conjugate eluted in void volume". The results obtained were

| Solution | OD 600 of peak one obtained after gel-filtration on Sephacryl HR S-300 | % conjugate eluted in the void volume after gel-filtration on Sephacryl HR S-500 |
|---|---|---|
| A | 3 | 28% |
| B | 2 | 24% |
| C | 1 | 10% |
| D | 0.6 | 20% |
| E | 1.7 | not tested |

EXAMPLE 6B

Coupling of Rabbit anti Human CRP to D VS-activated "Dex-Remazol Brilliant Red" conjugates in high ionic strength A solution of "Dex-Remazol Brilliant Red" conjugate was coupled with the Rabbit anti Human CRP immunoglobulin fraction (DAKO, Denmark, Cat. No. Q 0329).

"Dex-Remazol Brilliant Red" of peak MW 2,000,000 coupled 7 OD 530 Units/mg dextran as described for "Solution A" in Example 5B.

The following solution containing antibody and "Dex-Remazol Brilliant Red" was prepared:

0.00645 µmol antibody and 0.00129 µmol dextran (as "Dex-Remazol Brilliant Red") was mixed with 3.5 M potassium phosphate buffer, pH 8.8, to give the following final concentrations:
1.75 M potassium phosphate buffer
pH 8.6
0.57 mg antibody/ml
Molar ratio in the solution: "Dex-Remazol Brilliant Red"/ Antibody: 1/5

After mixing a precipitate was observed in the solution and coupling of the antibody was continued at 4–6° C. for 18 hours. After coupling, cysteine (Merck, Cat. No. 1.02838) was added to the samples to a final concentration of 0.01 M cysteine. The conjugate was dialysed for one hour against 0.1 M sodium chloride, 50 mM Tris adjusted to pH 9 with 1 M hydrochloric acid. After dialysis, Tween-20 was added to a final concentration of 1% v/v.

Free antibody and "Dex-Remazol Brilliant Red"-bound antibody in the sample was separated by gel-filtration on Sephacryl HR S-300 in 50 mM Tris, 0.1 M sodium chloride, 1% Tween-20 adjusted to pH 9 with 1 M hydrochloric acid. The flow rate was 1 ml/minute.

Separation on Sephacryl HR-S300 resulted in two peaks. Peak one from Sephacryl HR S-300 containing Rabbit anti Human CRP coupled to "Dex-Remazol Brilliant Red" is hereafter referred to as "Dex-Remazol Brilliant Red/a-CRP" conjugate. The Dex-Remazol Brilliant Red conjugate was collected as one fraction after 8 ml and OD 530 was measured:
OD 558 of peak one
obtained after gel-filtration
on Sephacryl HR S-300
1.67

From the given examples it can be derived that a primary targeting component can be coupled to a DVS activated dextran carrying two different dyes.

EXAMPLE 7

Devices and Uses of Cross-Linked Conjugate and Cross-Linked Conjugate Complexes

EXAMPLE 7A

The "Standard Lateral Flow Performance Test"

The following "Standard Lateral Flow Performance Test" is designed with the purpose of testing any coloured conjugate using a set of reproducible standard conditions and a commercially available antigen.

Materials:

| | |
|---|---|
| Nitrocellulose paper: | Millipore SRHF, 25 × 300 mm, Cat. No: SRHF 02020 |
| Glass fibre paper: | Whatman glass fibre paper with binder, 20 × 300 mm, Cat. No: 9599–9432 |
| Absorbent pad: | Whatman, 20 × 300 mm, cellulosic paper 3 mm, Cat No.: 3030–9433 |
| Plastic backing: | 0.01 White. Adhesives Research Inc. P.O. Box 100, Glen Rock, Pennsylvania, 17327, USA |
| Antigen: | Human serum Cross Reactive Protein (CRP) DAKO human serum calibrator, Cat. No: X 0925 |
| Antibody: | Rabbit anti human CRP, DAKO, Cat. No: Q 0329 |
| Coating buffer: | 0.1 M potassium phosphate buffer, pH 7.2 |
| Antigen buffer: | 50 mM Tris/HCl + 0.1 M NaCl + 0.5% Tween 20, pH 8.6 |

-continued

| | |
|---|---|
| Blocking buffer: | 50 mM Tris/HCl + 0.1 M NaCl + 0.5% Tween 20, pH 8.6 |
| Washing buffer: | 50 mM Tris/HCl + 0.1 M NaCl + 0.5% Tween 20, pH 8.6 |
| Conjugate buffer: | 50 mM Tris/HCl + 0.1 M NaCl + 0.5% Tween 20, pH 8.6 |
| Conjugate I: | "Dex-BSA-Rhodamine/aCRP" conjugate prepared according to present patent with 1.49 OD 558; prepared similar to Example 4A) |
| Conjugate II: | "Dex-BSA-Rhodamine/aCRP conjugate prepared according to WO 93/01498 with 1.74 OD 558 |

Methods

Preparation of lateral flow test strips:

The dry nitrocellulose paper is cut in strips (6 mm wide and 6 cm long) and mounted on a plastic backing (5 mm wide and 6 cm long). A glass fibre pad (5 mm wide, 20 mm long) is mounted at one end of the nitrocellulose strip. An absorbent pad (5 mm wide, 20 mm long) is mounted at the other end of the nitrocellulose strip.

Preparation of antibody solution:

Dilute rabbit anti human CRP to a final concentration of 0.125 mg immunoglobulin per ml of coating buffer.

Preparation of antigen solutions:

Prepare the following antigen solutions by dilution of the DAKO human serum calibrator in Antigen Buffer (the serum calibrator is diluted in accordance with the specified concentration of CRP in the calibrator):
A: 250 ng CRP/ml
B: 125 ng CRP/ml
C: 63 ng CRP/ml
D: 31 ng CRP/ml
E: 16 ng CRP/ml
F: 8 ng CRP/ml
G: 0 ng CRP/ml (negative control)

Preparation of conjugate solutions:

Prepare a dilution of Conjugate I and II to be tested in Conjugate buffer:

Conjugates: "Dex-BSA-Rhodamine/a-CRP" conjugate (from solution D in Example 4A) "Dex-Remazol Black/a-CRP" conjugate (from solution E in Example 6A)

Dilution: The conjugate is diluted to a final concentration having an absorbance of 0.7 when measured at the actual absorption maximum of the conjugate within the visible range of the absorption spectrum (i.e. within the range of about 450 nm to about 650 nm) using a 1 cm light path.

Performing the test:

1) Seven lateral flow test strips labelled A1, B1, C1, D1, E1, F1 and G1 have each applied 3 µl rabbit anti human CRP (0.125 mg immunoglobulin/ml) as a spot at the middle of the lateral flow test strip. Let the test strips dry for 15 min.

2) Block the remaining protein binding capacity of the test strips by application of 25 µl Blocking buffer at the upper end of the glass fibre pad on each test strip.

3) Wait for approx. 10 min. until the buffer by capillary flow has reached the absorbent pad at the other end of the test strips.

4) Apply 25 µl Antigen solution to each test strip at the upper end of the glass fibre pad. To the test strip labelled A1 is applied Antigen solution A (250 ng CRP/ml), to the test strip labelled B1 is applied Antigen solution B, etc. until the test strip labelled G1 to which is applied the negative control Antigen solution G. The Antigen solutions are added gradually to avoid "overflow" of the glass fibre pad.

5) Wait for 10 min. to let the Antigen solutions flow through to the absorbent pad at the other end of the test strip.

6) Add 25 μl Washing buffer to the lower end of the glass fibre pad on each test strip. Wait for 10 min. and add again 25 μl Washing buffer to the lower end of the glass fibre pad of each test strip.

7) Wait for 30 min.

8) Add 50 μl Conjugate I Dilution to the lower end of the glass fibre pad on each test strip.

9) Wait for 10 min.

10) Add 25 μl Washing buffer to the lower end of the glass fibre pad on each test strip. Wait for 10 min. and add again 25 μl Washing buffer to the lower end of the glass fibre pad of each test strip.

Repeat step 1 with a new set of lateral flow test strips labelled A2, B2, C2, D2, E2 and F2 and G2 go through steps 2–10 now using Conjugate II Dilution in step 8.

Evaluation of test results:

The colour intensity of the spots appearing on the test strips is evaluated by a scoring test. The following numbers are used the characterise the intensity of the appearing spot:

5: very intensely coloured spot
4: medium coloured spot
3: weakly coloured spot
2: spot barely seen
1: no spot can be detected Readings from the scoring test:

| Conjugate | Strip | Score |
|---|---|---|
| Conjugate I | A1 | 4 |
| | B1 | 4 |
| | C1 | 3 |
| | D1 | 2 |
| | E1 | 1 |
| | F1 | 1 |
| | G1 | 1 |
| Conjugate II | A2 | 1 |
| | B2 | 1 |
| | C2 | 1 |
| | D2 | 1 |
| | E2 | 1 |
| | F2 | 1 |
| | G2 | 1 |

EXAMPLE 7B

Standard Lateral Flow Performance Test with different "Dex-BSA-Rhodamine/a-CRP" conjugates Different "Dex-BSA-Rhodamine/a-CRP" conjugates were tested in the Standard Lateral Flow Performance Tests. All tests were performed as described in Example 7A.

The antigen concentration (CRP) in the test and the "Dex-BSA-Rhodamine/aCRP" conjugate concentration differ from test to test and will therefore be described separately for each test.

In all tests the antibody was spoiled on the nitrocellulose strip in a concentration of 0.1 mg antibody/ml and 1 μl was used for each spot.

Test no.1

The Lateral Flow Performance test was carried out with the "Dex-BSA-Rhodamine/a-CRP" conjugate from Example 4A, solution C.

The Lateral Flow Performance test was carried out with using the following conjugate fractions:

| | | |
|---|---|---|
| I: | Peak one from Sephacryl HR S-300 | Concentration: OD 558 = 0.1 |
| II: | Fraction one from Sephacryl HR S-500 | Concentration: OD 558 = 0.1 |
| III: | Fraction two from Sephacryl HR S-500 | Concentration: OD 558 = 0.1 |

The colour intensity of the spots appearing on the test strips is measured by the use of a Flatbed scanner from AGFA, ARUS II with the following set up conditions:

| | |
|---|---|
| Original: | Reflective |
| Mode: | Gray-scale |
| Input: | 240 dpi |
| Scale to: | 100% |
| Range: | Histogram Min = 130, Max = 254 |
| ToneCurve: | None |
| Sharpness: | None |
| Descreen: | None |
| size: | A4 portrait |

The software CREAM for windows (1-D, Kem-En-Tec ANS, Copenhagen, Denmark, Cat. (No. 990012) was used for calculation of the results which are given in intensity units.

Results:

| Antigen concentration ng CRP/ml | Reading Conjugate I | Reading Conjugate II | Reading Conjugate III |
|---|---|---|---|
| 250 | 1147 | 1848 | 928 |
| 125 | 752 | 1447 | 684 |
| 63 | 426 | 880 | 408 |
| 31 | 299 | 538 | 265 |
| 16 | 140 | 527 | 142 |
| 0 | 66 | 66 | 66 |

Conclusion:

The conjugate collected in fraction one from Sephacryl HR S-500 (collected from 7 to 10.5 ml) gives a significant better response than the conjugate collected in fraction two (collected from 10.5 to 18 ml). Test of peak one from Sephacryl HR S-300 which includes the two fractions from Sephacryl S-500 gives almost the same response as fraction two obtained from Sephacryl HR S-500. The above-given test results illustrates the advantage of using water-soluble, high molecular weight conjugates, i.e. conjugates which are totally or almost totally excluded from the volume when gel-filtered on a Sephacryl HR S-500 column.

Test no. 2

The Lateral Flow Performance test was carried out with the "Dex-BSA-Rhodamine/a-CRP" conjugate from Example 4B.

The performance of the above-mentioned conjugate was compared with a reference conjugate (prepared with DVS activated dextran), "Dex-BSA-Rhodamine/a-CRP" from Example 4A, solution E.

I: "Dex-BSA-Rhodamine/a-CRP", Example 4B
II: "Dex-BSA-Rhodamine/a-CRP", Example 4A, solution E (reference)
Conjugate concentration: OD 558=0.5
Results:

| Antigen concentration ng CRP/ml | Reading Conjugate I | Reading Conjugate II (reference) |
|---|---|---|
| 250 | 2844 | 2184 |
| 125 | 2736 | 1778 |
| 63 | 1916 | 1136 |
| 31 | 980 | 527 |
| 16 | 592 | 363 |
| 0 | 66 | 66 |

Conclusion:

The above test results demonstrates the feasibility to use EPCH-activated carrier moieties as the basis for high molecular weigh conjugates with a performance similar to, or better than, conjugates based on DVS-activated carrier moieties.

Test no. 3

The Lateral Flow Performance Test was carried out with the "Dex-BSA-Rhodamine/a-CRP" conjugates from Example 4F (prepared in high (solution A) and low (solution B) ionic strength, respectively). The various fractions collected from gel-filtration on Sephacryl HR S-1000 and the reference conjugate from Example 4A, solution E, were also tested:

I: "Dex-BSA-Rhodamine/a-CRP", Ex. 4F, solution A OD 558=0.35
II: "Dex-BSA-Rhodamine/a-CRP", Ex. 4F, solution B OD 558=0.5
III: "Dex-BSA Rhodamine/a-CRP", Ex. 4A, solution E (reference) OD 558=0.5
IV: Fraction 1 (Sephacryl S-1000) from solution A, collected from 8–10 ml
V: Fraction 2 (Sephacryl S-1000) from solution A, collected from 10–12 ml
VI: Fraction 3 (Sephacryl S-1000) from solution A, collected from 14–16 ml
VII: Fraction 4 (Sephacryl S-1000) from solution A, collected from 18–20 ml The fractions IV–VII were tested using a concentration of OD 558=0.35.
Results:

| Antigen concentration ng CRP/ml Reference | Reading Conjugate A High ionic strength | Reading Conjugate B Low ionic strength | Reading |
|---|---|---|---|
| 250 | — | 148 | 2184 |
| 125 | — | 66 | 1778 |
| 63 | 709 | 66 | 1136 |
| 31 | 542 | 66 | 527 |
| 16 | 425 | 66 | 363 |
| 8 | 173 | 66 | 66 |
| 4 | 154 | 66 | 66 |
| 0 | 66 | 66 | 66 |

Test of fractions collected from Sephacryl HR S1000:

| Antigen concentration ng CRP/ml | Reading Fraction 1 | Reading Fraction 2 | Reading Fraction 3 | Reading Fraction 4 |
|---|---|---|---|---|
| 63 | 2416 | 1052 | 612 | 481 |
| 31 | 1854 | 624 | 485 | 176 |
| 16 | 1064 | 501 | 214 | 66 |
| 8 | 623 | 430 | 66 | 66 |
| 4 | 527 | 180 | 66 | 66 |
| 0 | 66 | 66 | 66 | 66 |

Conclusion:

This test results demonstrate that conjugates produced by coupling of antibody at low ionic strength (conjugate B), i.e. without (reversible) precipitating the reactants give very poor performance when compared to conjugates where the coupling of antibody has been performed under reversible precipitation conditions (conjugate A). These results are in agreement with the fact that conjugate B has a significant lower molecular weight than conjugate A. Furthermore, it can be seen that when a conjugate is fractionated into samples of decreasing molecular weight, the performance of the samples decreases with he molecular weight, i.e. high molecular weight conjugates give higher performance.

EXAMPLE 7C

Standard Lateral Flow Performance Test with different "Dex-BSA-Dye-/a-CRP" and "Dex-Dye-/a-CRP" conjugates Different"Dex-BSA-Dye/a-CRP" and "Dex-Dye/a-CRP" conjugates were tested in the Standard Lateral Flow Performance Test. All tests were performed as described in Example 7A.

The antibody concentration used for the dot, the volume ($\mu$l) of antibody used for spotting on the nitrocellulose strip, the antigen concentration (CRP) and the conjugate concentrations differ from test to test and will therefore be described separately for each test.

Test no. 1

The Lateral Flow Performance Tests was carried out with the "Dex-Remazol Black/a-CRP" conjugates from Example 6A, solution A, B and C.

The performance of the conjugates were compared with a reference conjugate, "Dex-BSA-Rhodamine/a-CRP" from Example 4A, solution E.

The Lateral Flow Performance Tests were made using the following conditions:

3 $\mu$l antibody in a concentration of 1 mg/ml was used for spots when testing the "Dex-Remazol Black/a-CRP" conjugates, and 1 $\mu$l antibody in a concentration of 0.1 mg/ml was used when testing the reference "Dex-BSA-Rhodamine/a-CRP" conjugate.

I: "Dex-Remazol Black/a-CRP", conjugate A  OD 600 = 0.6
II: "Dex-Remazol Black/a-CRP", conjugate B  OD 600 = 0.6
III: "Dex-Remazol Black/a-CRP", conjugate C  OD 600 = 0.6
IV: "Dex-BSA Rhodamine/a-CRP", Ex. 4A, solution E (reference)  OD 558 = 0.5

Results:

| Antigen concentration ng CRP/ml | Reading Conjugate A | Reading Conjugate B | Reading Conjugate C | Reading Reference |
|---|---|---|---|---|
| 250 | 989 | 705 | 338 | 2184 |
| 0 | 66 | 66 | 66 | 66 |

The test results demonstrate the feasibility to use Remazol-Black as a signal component.

Test no. 2

The Lateral Flow Performance Tests was carried out with the "Dex-BSA-Uniblue A/a-CRP" conjugates from Example 4E, solution A and B.

The performance of the conjugates were compared with a reference conjugate, "Dex-BSA-Rhodamine/a-CRP" from Example 4A, solution E.

The Lateral Flow Performance Tests were made using the following conditions:

1 µl antibody in a concentration of 0.1 mg/ml was used for spots when testing the "Dex-BSA-Uniblue A/a-CRP" conjugates and the reference "Dex-BSA-Rhodamine/a-CRP" conjugate.

| | |
|---|---|
| I: "Dex-BSA-UniblueA/a-CRP", conjugate A | OD 595 = 0.5 |
| II: "Dex-BSA-UniblueA/a-CRP", conjugate B | OD 595 = 0.5 |
| III: "Dex-BSA Rhodamine/a-CRP", Ex. 4A, solution E (reference) | OD 558 = 0.5 |

Results:

| Antigen concentration ng CRP/ml | Reading Conjugate A | Reading Conjugate B | Reading Reference |
|---|---|---|---|
| 250 | 1158 | 1062 | 2184 |
| 0 | 121 | 87 | 66 |

The test results demonstrate the feasibility to use Uniblue A as a signal component.

Test no.3

The Lateral Flow Performance Tests was carried out with the "Dex-Remazol Brilliant Red/a-CRP" conjugate from Example 6B.

The performance of the conjugate was compared with a reference conjugate, "Dex-BSA-Rhodamine/a-CRP" from Example 4A, solution E.

The Lateral Flow Performance Tests were made using the following conditions:

3 µl antibody in a concentration of 1 mg/ml was used for spots when testing the "Dex-Brilliant Red/a-CRP" conjugates, and 1 µl antibody in a concentration of 0.1 mg/ml was used when testing the reference "Dex-BSA-Rhodamine/a-CRP" conjugate.

| | |
|---|---|
| I: "Dex-Remazol Brilliant Red/a-CRP" | OD 530 = 1.0 |
| II: "Dex-BSA Rhodaminela-CRP", Ex. 5A, solution E (reference) | OD 558 = 0.5 |

Results:

| Antigen concentration ng CRP/ml | Reading Conjugate | Reading Reference |
|---|---|---|
| 125 | 231 | 1778 |
| 0 | 66 | 66 |

The test results demonstrate the feasibility to use Remazol Brilliant Red as a signal component.

From the given examples it can be derived that reversible precipitation conditions give conjugates coupled with antibody and dye, with and without a spacer component, that show a better performance in lateral flow test strips than conjugates prepared without reversible precipitation conditions.

What is claimed is:

1. A method for the preparation of a water-soluble cross-linked conjugate comprising moieties of at least one carrier component, moieties of more than one linking component, moieties of at least one spacer component, moieties of at least one signal component and moieties of at least one primary targeting component, the signal component being covalently attached to the spacer component and the spacer component being covalently attached, via the linking component, to the carrier component, said method comprising:

a) reacting a water-soluble intermediate conjugate comprising moieties of at least one carrier component, moieties of more than one linking component, moieties of at least one spacer component, moieties of at least one signal component, the signal component being covalently attached to the spacer component and the spacer component being covalently attached, via the linking component, to the carrier component, via reaction of unreacted reactive moieties derived from the linking component, with at least one primary targeting component in an aqueous solution, the conditions being such that a reversible precipitate is formed;

b) re-dissolving the reversible precipitate comprising the water-soluble cross-linked conjugate in an aqueous medium; and c) optionally subjecting the water-soluble cross-linked conjugate to a purification step.

2. A method for the preparation of a water-soluble cross-linked conjugate comprising moieties of at least one carrier component, moieties of more than one linking component, moieties of at least one signal component and moieties of at least one primary targeting component, the signal component being covalently attached, via the linking component, to the carrier component, said method comprising:

a) reacting a water-soluble intermediate conjugate comprising moieties of at least one carrier component, moieties of more than one linking component, moieties of at least one signal component, the signal component being covalently attached, via the linking component, to the carrier component, via reaction of unreacted reactive moieties derived from the linking component, with at least one primary targeting component in an aqueous solution, the conditions being such that a reversible precipitate is formed;

b) re-dissolving the reversible precipitate comprising the water-soluble cross-linked conjugate in an aqueous medium; and c) optionally subjecting the water-soluble cross-linked conjugate to a purification step.

3. A method according to claim 1, wherein the precipitation step a) is performed by salting-out by means of a lyotropic salt present in a concentration of at least 1.25 M.

4. A method according to claim 3, wherein said lyotropic salt is selected from the group consisting of sulphates, phosphates, citrates and tartrates of lithium, sodium, potassium, calcium and ammonium, and mixtures thereof.

5. A method according to claim 1, wherein the precipitation step a) is carried out at a pH above 6.

6. A method according to claim 1, wherein the carrier component is selected from the groups consisting of dextrans, including carboxymethyl-dextrans; starches, including hydroxyethyl-starches and hydroxypropyl-starches; glycogen; agarose derivatives; cellulose derivatives; natural gums; and mixtures thereof.

7. A method according to claim 6, wherein the carrier component is dextran.

8. A method according to claim 1, wherein the linking component selected from the group consisting of divinyl sulfone and epichlorohydrin.

9. A method according to claim 1, wherein the linking component is divinyl sulfone.

10. A method according to claim 1, wherein the spacer component is selected from the group consisting of proteins and polypeptides.

11. A method according to claim 1 wherein the spacer component is selected from the group consisting of BSA, ovalbumin and globulin.

12. A method according claim 1, wherein the signal component is a dye.

13. A method according claim 1, wherein said water-soluble cross-linked conjugate has a water solubility of at least 10 mg dry conjugate per ml water at 25° C.

14. A method for the preparation of a water-soluble cross-linked conjugate complex comprising a conjugate prepared according to claim 1, a ligand and a secondary targeting component, the ligand being covalently bound to the secondary targeting component, and the ligand being bound to the primary targeting component of the conjugate by means of non-covalent bonds, said method comprising:

I) preparing a water-soluble cross-linked conjugate according to any of the preceding claims;

II) reacting the optionally purified water-soluble cross-linked conjugate with a ligand, said ligand being covalently bound to a secondary targeting component, in an aqueous solution;

III) terminating the reaction.

15. A method according to claim 14, wherein step III) is carried out by addition of an excess of free ligand.

16. A water-soluble cross-linked conjugate obtained by the method defined in any of the claims 1–13.

17. A water-soluble cross-linked conjugate complex obtained by the method defined in any of the claims 14–15.

18. A lateral flow device for determining the presence or absence of at least one target component in a liquid sample, said lateral flow device comprising:

I) a test strip comprising an application part, a deposit part and a detection part and being arranged in such a way that the liquid sample can flow from the application part through the deposit part to the detection part;

II) a dry deposit, located in the deposit part of the test strip, of at least one conjugate prepared by the method of claim 1, or a mixture thereof; and III) at least one targeting component capable of selectively binding to, or selectively reacting with, one or more target components present in the liquid sample, the targeting component being immobilised on the detection part of the test strip.

19. A method for determining the presence or absence of at least one target component in a liquid sample, said method comprising:

I) adding the liquid sample to the application part of a lateral flow device as defined in claim 18;

II) optionally adding a washing buffer to the application part of the lateral flow device;

III) allowing sufficient time for the applied liquid, and where appropriate the washing buffer, to flow from the application part through the deposit part to the detection part where the at least one targeting component is allowed to selectively bind to, or selectively reacting with, any target component present in the liquid sample to form a detectable complex; and IV) detecting the presence or absence of a signal component or signal component precursor in the detection part, said presence or absence of a signal component or signal component precursor being indicative of the presence or absence of the at least one target component in the liquid sample.

20. A method according to claim 19, wherein the signal is directly detectable by the naked eye.

21. A method according to claim 20, wherein the signal is detectable by the naked eye after addition of a reagent to the detection part.

22. A method according to claim 19, wherein the liquid sample is of biological origin.

23. A method according to claim 22, wherein the liquid sample is a blood sample, a serum sample, a plasma sample, a urine sample, a semen sample, or mixtures thereof.

24. A method for targeting a target component in immunochemical assay techniques, immunohistochemical procedures, cytochemical procedures, flow cytometry, in situ hybridisation techniques, membrane hybridisation techniques, biosensors, lateral flow devices, or methods based on lectin/carbohydrate interactions, said method comprising allowing at least one targeting component of a water-soluble cross-linked conjugate as defined in claim 16 to selectively bind to, or selectively react with, the target component.

25. A method for targeting a target component in immunochemical assay techniques, immunohistochemical procedures, cytochemical procedures, flow cytometry, in situ hybridisation techniques, membrane hybridisation techniques, biosensors, lateral flow devices, or methods based on lectin/carbohydrate interactions, said method comprising allowing at least one targeting component of a water-soluble cross-linked conjugate complex as defined in claim 17 to selectively bind to, or selectively react with, the target component.

* * * * *